United States Patent [19]

Bogden et al.

[11] Patent Number: 5,217,955

[45] Date of Patent: Jun. 8, 1993

[54] TREATMENT OF CANCER WITH PEPTIDE ANALOG OF BOMBESIN, GRP, LITORIN OR NEUROMEDIN

[75] Inventors: Arthur E. Bogden, Hopedale; Jacques-Pierre Moreau, Upton, both of Mass.

[73] Assignee: Biomeasure, Inc., Milford, Mass.

[21] Appl. No.: 520,225

[22] Filed: May 9, 1990

Related U.S. Application Data

[63] Continuation-in-part of Ser. No. 440,039, Nov. 21, 1989, abandoned, which is a continuation-in-part of Ser. No. 408,125, Sep. 15, 1989, abandoned.

[51] Int. Cl.$^5$ .......................... C07K 7/06; C07K 7/08; C07K 7/10
[52] U.S. Cl. ........................................ 514/12; 514/13; 514/14; 514/15
[58] Field of Search .................................... 514/12-15

[56] References Cited

PUBLICATIONS

Rivier et al., "Bombesin, Bombesin Analogues, and Related Peptides: Effects on Thermoregulation", 17:1767, 1978.
Cuttitta et al., "Autocrine growth factors in human small cell lung cancer", Cancer Surveys 4:708, 1985.
Zachary et al., "High-affinity receptors for peptides of the bombesin family in Swiss 3T3 cells," Proc. Natl. Acad. Sci. USA, 82:7616, Nov. 1985.
Heinz-Erian et al., "Bombesin analogues: a new class of bombesin receptor antagonsits", pp. G439-G442.
Martinez et al., "Synthesis and Biological Activities of Some Pseudo-Peptide Analogues of Tetragastrin: The Importance of the Peptide Backbone", J. Med. Chem. 1985, 28:1874-1879.
Aumelas et al., "$^1$H and $^{13}$C n.m.r. studies of pseudo--peptide analogues of the C-terminal tetrapeptide of gastrin", Int. J. Peptide Protein Res., 1987, 30:596-604.
Dubreuil et al., "Degradation of a Tetragastrin Analogue by a Membrane Fraction from Rat Gastric Mucosa", Drug Design and Delivery, 1987, 2:49-54.
Gargosky et al., "C-Terminal bombesin sequence requirements for binding and effects on protein synthesis in Swiss 3T3 cells", Biochem. J., 1987, 247:427-432.
Heikkila et al., "Bombesin-related peptides Induce Calcium Mobilization in a Subset of Human Small Cell Lung Cancer Cell Lines", The Journal of Biological Chemistry, 1987, 262:16456-16480.
Alexander et al., "Effects of Bombesin on Growth of Human Small Cell Lung Carcinoma in Vivo", Cancer Research, 1988, 48:1439-1441.
Rossowski et al., "Effects of a Novel, Potent Bombesin Antagonist Analogue on Bombesin-Stimulated Gastric Gastric Acid Secretion and Growth Hormone Release in the Pentobarbital-Anesthetized Rat.," 1988 Abstract.
Leij et al., "Recombinant Interleukin-2 Stimulated Lymphocytes in Peripheral Blood as Effector Cells for of Cell Lysis in Small-Cell Lung Carcinoma," 1988, 132:1223.
Heimbrook et al., "Elucidation of a Novel Gastrin Releasing Peptide Antagonist", (to be published in: Synthetic Peptides: Approaches to Biological Problems, vol. 86.
Woll et al., "Bombesin is a Specific Receptor Antagonist in Swiss 3T3 Cells", Biochemical and Biophysical Research Communications, 1988, 155:359-365.
Caranikas et al., "Synthesis and Biological Activities of Substance P Antagonists", J. Med. Chem. 1982, 25:1313-1316.

(List continued on next page.)

[57] ABSTRACT

A method of treating cancer in a human patient, the method involving administering to the patient a cancer cell inhibiting amount of an analog of a naturally occurring biologically active peptide or a fragment thereof, the peptide being one of mammalian gastrin-releasing peptide, neuromedin B, neuromedin C, amphibian bombesin, or litorin.

41 Claims, 9 Drawing Sheets

OTHER PUBLICATIONS

Rosell et al., "Substance P-Antagonist: a new type of pharmacological tool", *Trends in Pharmacological Sciences* 1982, 3;211–212.

Lundberg et al., "A substance P antagonist inhibits vagally induced increase in vascular permeability and bronchial smooth muscle contraction in the guinea pig", *Proc. Natl. Acad. Sci. USA* 1983, 80:1120–1124.

Engberg et al., "A synthetic peptide as an antagonist of substance P", *Nature* 1981, 293:222–223.

Mizrahi et al., "Substance P Antagonists Active in vitro and in vivo", *European Journal of Pharmacology*, 1982, 82:101–105.

Leander et al., "Aspecific substance P antagonist blocks smooth muscle contractions induced by non-cholinergic, non-adrenergic nerve stimulation", *Nature* 1981, 294:467–469.

*Primary Examiner*—Lester L. Lee
*Attorney, Agent, or Firm*—Fish & Richardson

FIG. 9

Litorin

```
A1    A2    A3    A4    A5    A6    A7    A8    A9
pGlu-Gln-Trp-Ala-Val-Gly-His-Phe-Met
```

Neuromedin B

```
A0    A1    A2    A3    A4    A5    A6    A7    A8    A9
Gly-Asn-Leu-Trp-Ala-Thr-Gly-His-Phe-Met
```

Neuromedin C

```
A0    A1    A2    A3    A4    A5    A6    A7    A8    A9
Gly-Ser-His-Trp-Ala-Val-Gly-His-Leu-Met
```

Bombesin (last 10 amino acids)

```
A0    A1    A2    A3    A4    A5    A6    A7    A8    A9
Gly-Asn-Gln-Trp-Ala-Val-Gly-His-Leu-Met
``` human GRP (last 10 amino acids)

```
A0    A1    A2    A3    A4    A5    A6    A7    A8    A9
Gly-Asn-His-Trp-Ala-Val-Gly-His-Leu-Met
```

TREATMENT OF CANCER WITH PEPTIDE ANALOG OF BOMBESIN, GRP, LITORIN OR NEUROMEDIN

BACKGROUND OF THE INVENTION

This application is a continuation-in-part of U.S. Ser. No. 440,039, filed Nov. 21, 1989 and now abandoned, which is a continuation-in-part of U.S. Ser. No. 408,125, filed Sep. 15, 1989 and now abandoned.

This invention relates to the treatment of benign or malignant proliferation of tissue.

The amphibian peptide bombesin, pGlu-Gln-Arg-Leu-Gly-Asn-Gln-Trp-Ala-Val-Gly-His-Leu-Met-$NH_2$ (Anastasi et al., Experientia 27:166-167 (1971)), is closely related to the mammalian gastrin-releasing peptides (GRP), e.g., the porcine GRP, $H_2N$-Ala-Pro-Val-Ser-Val-Gly-Gly-Gly-Thr-Val-Leu-Ala-Lys-Met-Tyr-Pro-Arg-Gly-Asn-His-Trp-Ala-Val-Gly-His-Leu-Met-($NH_2$) (McDonald et al., Biochem. Biophys. Res. Commun. 90:227-233 (1979)) and human GRP, $H_2N$-Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met ($NH_2$). Bombesin has been found to be a growth factor for a number of human cancer cell lines, including small-cell lung carcinoma (SCLC), and has been detected in human breast and prostate cancer (Haveman et al., eds. *Recent Results in Cancer Research - Peptide Hormones in Lung Cancer,* Springer-Verlag, New York:1986). A number of these cancers are known to secrete peptide hormones related to GRP or bombesin. Consequently, antagonists to bombesin have been proposed as agents for the treatment of these cancers.

Cuttitta et al. demonstrated that a specific monoclonal antibody to bombesin inhibited in vivo the growth of a human small-cell lung cancer cell line xenografted to nude mice (Cuttitta et al., Cancer Survey 4:707-727 (1985)). In 3T3 murine fibroblasts which are responsive to the mitotic effect of bombesin, Zachary and Rozengurt observed that a substance P antagonist (Spantide) acted as a bombesin antagonist (Zachary et al., proc. Natl. Acad. Sci. (U.S.A.), 82:7616-7620 (1985)). Heinz-Erian et al. replaced His at position 12 in bombesin with D-Phe and observed bombesin antagonist activity in dispersed acini from guinea pig pancreas (Heinz-Erian et al., Am. J. of Physiol. 252:G439-G442 (1987)). Rivier reported work directed toward restricting the conformational freedom of the bioactive C-terminal decapeptide of bombesin by incorporating intramolecular disulfide bridges; however, Rivier mentioned that, so far, bombesin analogs with this modification fail to exhibit any antagonist activity (Rivier et al., "Competitive Antagonists of Peptide Hormones," in Abstracts of the International Symposium on Bombesin-Like Peptides in Health and Disease, Rome, Italy (October, 1987).

Bombesin exhibits both direct and indirect effects on the gastrointestinal tract, including the release of hormones and the stimulation of pancreatic, gastric, and intestinal secretion and of intestinal mobility. Gastrin and cholecystokinin (CCK) which are released by bombesin, have been shown to play a role in the maintenance of normal gastrointestinal mucosa as well as in augmenting growth of normal and neoplastic tissues. The growth of xenografted human colon and stomach carcinomas in nude mice has been stimulated by the administration of gastrin and later inhibited with the addition of secretin (Tanake et al., 1986, Tokaku J. Exp. Med. 148:459) and the growth of MC-26 murine colon carcinoma, which possesses gastrin receptors is stimulated by pentagastrin (Winsett et al., 1980, Surgery 99:302, and inhibited by proglumide, a gastrin-receptor anagonist, Beauchamp et al., 1985, Ann. Surg. 202:303. Bombesin has been found to act concurrently as both a trophic agent for normal host pancreas and a growth inhibitory agent in xenografted human pancreatic tumor tissue, Alexander et al., 1988, Pancreas 3:247.

Abbreviations (uncommon):
cyclohexly-Ala = CHx—Ala    (cyclohexyl alanine)

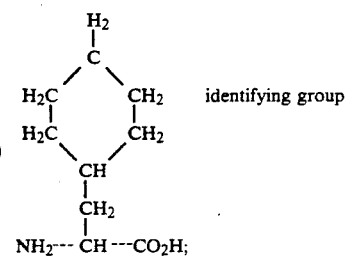

pGlu = (pyroglutamic acid);

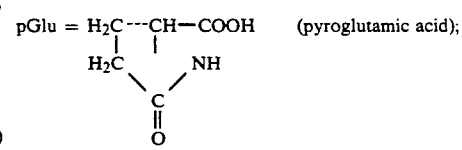

Nle = (norleucine)

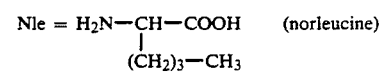

Pal = 3-pyridyl-alanine
β-leu = β - homoleucine
γ-leu = gamma -homoleucine
D-Cpa = D-para-chloro-phenylalanine
HyPro = hydroxyproline
Nal = naphthylalanine
Sar = saracosine
$F_5$—Phe = penta-fluoro-phenylalanine Sta (statine) = (3S,4S)-4-amino-3-hydroxy-6-methylheptanoic acid, and has the chemical structure:

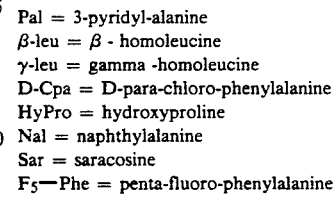

AHPPA = (3S,4S)-4-amino-3-hydroxy-5-phenylpentanoic acid, and has the chemical structure:

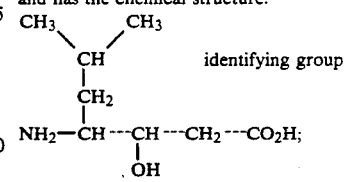

ACHPA = (3S,4S)-4-amino-5-cyclohexyl-3-hydroxypentanoic acid and has the chemical structure:

-continued

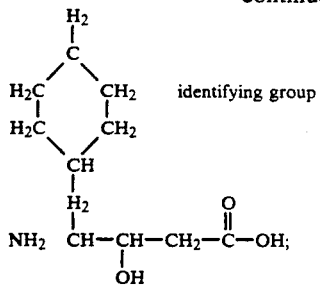  identifying group

R = right (D) configuration; S = left (L) configuration;
racemate = equal mix of R and S
1-methyl-His; 3-methyl-His = methyl ($CH_3$) group on
nitrogen at positions 1 or 3 of Histidine:

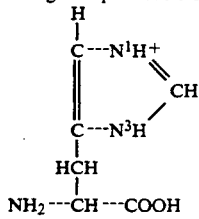

SUMMARY OF THE INVENTION

In one aspect, the invention features a method of treating non-malignant proliferative disease in a human patient, by administering to the patient a disease inhibiting amount of an analog (i.e., linear or cyclic) of a naturally occurring biologically active peptide, the peptide being one of mammalian gastrin-releasing peptide (GRP), neuromedin B, neuromedin C, amphibian bombesin, or litorin.

In preferred embodiments, the disease may be the proliferation of smooth muscle.

In another aspect, the invention features a method of treating cancer in a human patient, by administering to the patient a cancer cell inhibiting amount of an analog (i.e., linear or cyclic) of a naturally occurring biologically active peptide, the peptide being one of mammalian gastrin-releasing peptide (GRP), neuromedin B, neuromedin C, amphibian bombesin, or litorin.

Preferably, the method includes the treatment of prostatic, colon, breast, pancreatic, or lung cancer.

Preferably, for both aspects of the invention, the analog may be an agonist or an antagonist of the naturally occurring biologically active peptide; preferably, the analog is at least 25%, more preferably 50% or 75%, homologous with a region of the naturally occurring peptide. As used herein, an "agonist" mimics or enhances the biological effect of the natural peptide on its target cell and a "partial agonist" mimics or enhances the biological effect of the natural peptide, but to a lesser extent than an agonist. Biological effect, as used herein, is measured by the effect of the natural peptide in one of two systems an in vitro pancreatic amylase release assay and an in vitro 3T3 fibroblast cell division system, both of which are described in European Patent Application 88308916.6, hereby incorporated by reference. An agonist will stimulate the effect of the natural peptide on either amylase release from pancreatic cells or fibroblast cell division by 100%, whereas a partial agonist will have a lesser stimulatory effect, i.e., ranging between 0–99%.

Preferably, the analog administered according to methods of the invention may be either a linear or a cyclic analog, which includes between seven and ten amino acid residues, inclusive, of one of the following naturally occurring peptides which terminate at the carboxy terminus with a Met residue: (a) litorin; (b) the ten amino acid carboxy-terminal region of mammalian GRP, neuromedin B, or neuromedin C; and (c) the ten amino acid carboxy terminal region of amphibian bombesin, and the analog is of the formula (I):

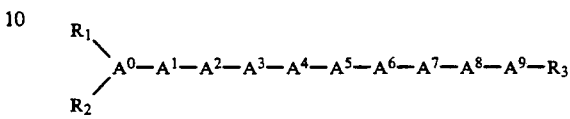

wherein $A^0$=Gly, D- or L- isomer of any of pGlu, Nle, α-aminobutyric acid, Ala, Val, Gln, Asn, Leu, Ile, p-X--Phe (where X=H, F, Cl, Br, $NO_2$, OH, $CH_3$), Trp, or β-Nal, or is deleted;

$A^1$=the D- or L-isomer of any of pGlu, Nle, α-aminobutyric acid, Ala, Val, Gln, Asn, Leu, Ile, p X-Phe (where X=H, F, Cl, Br, $NO_2$, OH, or $CH_3$), Asp, Glu, $F_5$-Phe, Trp, β-Nal, Cys, Lys, or is deleted;

$A^2$=Gly, D- or L- isomer of any of pGlu, Ala, Val, Gln, Asn, Leu, Ile, p-X-Phe (where X=H, F, Cl, Br, $NO_2$, OH, or $CH_3$), Trp, β-Nal, Asp, Glu, His, 1-methyl-His 3-methyl-His, Cys, Lys, or is deleted;

$A^3$=the D- or L-isomer of any of p-X-Phe (where X=H, F, Cl, Br, $NO_2$, OH, or $CH_3$), β-Nal, or Trp;

$A^4$=Ala, Val, Gln, Asn, Gly, Leu, Ile, Nle, α-aminobutyric acid, p-X-phe (where X=H, F, Cl, Br, $NO_2$, OH, or $CH_3$), Trp, or β-Nal;

$A^5$=Gln, Asn, Gly, Ala, Leu, Ile, Nle, α-aminobutyric acid, Val, p-X-Phe (where X=H, F, Cl, Br, $NO_2$, OH, or $CH_3$), Trp, Thr, or β-Nal;

$A^6$=Sar, Gly or the D-isomer of any Ala, N-methyl-Ala, Val, Gln, Asn, Leu, Ile, p-X-Phe (where X=H, F, Cl, Br, $NO_2$, OH, or $CH_3$), Trp, Cys, or β-Nal;

$A^7$=1-methyl-His, 3-methyl-His, His, Lys, Asp, or Glu;

$A^8$=Leu, Ile, Val, Nle, α-aminobutyric acid, p-X-Phe (where X=H, F, Cl, Br, $NO_2$, OH, or $CH_3$), Trp, Thr, β-Nal, Lys, Asp, Glu, CHx-Ala, or Cys;

$A^9$=L-isomer of any of Met, Met-oxide, Leu, Ile, Nle, α-aminobutyric acid, p-X-Phe (where X=H, F, Cl, Br, $NO_2$, OH, or $CH_3$), Trp, β-Nal, CHx-Ala, or Cys; each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkinyl, phenyl, naphthyl, or $C_{7-10}$ phenylalkyl), or $C_1$–$C_{12}$ acyl, and $R_1$ and $R_2$ are bonded to the N-terminal amino acid of the peptide; provided that when one of $R_1$ or $R_2$ is $COE_1$, the other must be H; and $R_3$ is H, $NH_2$, $C_{1-12}$ alkyl, $C_{7-10}$ phenylalkyl, or $C_{3-20}$ naphthylalkyl; and further provided that, if $A^0$ is present, $A^1$ cannot be pGlu; and, if $A^0$ or $A^1$ is present, $A^2$ cannot be pGlu; and further provided that, when $A^0$ is deleted and $A^1$ is pGlu, $R_1$ must be H and $R_2$ must be the portion of Glu that forms the imine ring in pGlu; and further provided that, where $A^0$ is deleted and $A^1$ is not pGlu, $A^1$ may be bonded to $A^9$, or where $A^0$ and $A^1$ are deleted and $A^2$ is not pGlu, $A^2$ may be bonded to $A^9$, or where $A^0$, $A^1$ and $A^2$ are deletd, $A^3$ can be bonded to $A^9$ to form a cyclized peptide; and provided that where $A^0$ is deleted and $A^1$ is Asp or Glu, or where $A^0$ and $A^1$ are deleted and $A^2$ is Asp or Glu, either $A^1$ or $A^2$ can be bonded with $A^7$ or $A^8$, where $A^7$ or $A^8$ is Lys, or where $A^0$ is deleted and $A^1$ is Lys or $A^0$ and $A^1$ are deleted and $A^2$ is Lys, either $A^1$ or $A^2$ can be bonded to $A^7$ or $A^8$, where $A^7$ or $A^8$ is Asp or Glu; and further provided that either one of $A^1$ or $A^2$ can be Cys and can be bonded through a disulfide bridge with either $A^8$ or $A^9$, provided that either one of $A^8$ or $A^9$ can be Cys and can be bonded through a disulfide bridge with either $A^1$ or $A^2$; and further provided that where $A^0$ and $A^1$ are deleted and $A^6$ is D-Ala, $A^8$-$A^9$ cannot be Leu-Met-$NH_2$; or a pharmaceutically acceptable salt thereof.

More preferably, the analog of formula (I) above is of the formula:

$A^0$=pGlu, Gly, D-Phe, or is deleted;
$A^1$=pGlu, D-Phe, D-Ala, D-$\beta$-Nal, D-Cpa, D-Asn, Cys, or is deleted;
$A^2$=pGlu, Asn, Gln, His, 1-methyl-His, 3-methyl-His, Cys or is deleted;
$A^3$=Trp;
$A^4$=Ala;
$A^5$=Val;
$A^6$=Sar, Gly, D-Phe, or D-Ala;
$A^7$=His;
$A^8$=Leu, Phe, Chx-Ala, or Cys;
$A^9$=L-isomer of any of Met, Leu, Ile, Nle, Phe, or Cys.

Examples of preferred peptide analogs are:

pGlu—Gln—Trp—Ala—Val—Gly—His—Leu—Leu—$NH_2$;
D—Phe—Gln—Trp—Ala—Val—Gly—His—Leu—Leu—$NH_2$;
D—Phe—Gln—Trp—Ala—Val—Gly—His—Leu—Met—$NH_2$;
D—Cpa—Gln—Trp—Ala—Val—Gly—His—Leu—Met—$NH_2$;
D—Cpa—Gln—Trp—Ala—Val—Gly—His—Leu—Leu—$NH_2$;
D—Phe—Gln—Trp—Ala—Val—D—Ala—His—Leu—Leu—$NH_2$;
D—Phe—Gln—Trp—Ala—Val—D—Ala—His—Leu—Met—$NH_2$;
D—Cpa—Gln—Trp—Ala—Val—D—Ala—His—Leu—Met—$NH_2$;
pGlu—Gln—Trp—Ala—Val—Gly—His—Phe—Leu—$NH_2$;
D—Phe—Gln—Trp—Ala—Val—Gly—His—Phe—Leu—$NH_2$;
D—Phe—Gln—Trp—Ala—Val—D—Ala—His—Phe—Met—$NH_2$;
D—Phe—Gln—Trp—Ala—Val—D—Ala—His—Phe—Leu—$NH_2$;
D—Phe—Gln—Trp—Ala—Val—Gly—His—CHx—Ala—Leu—$NH_2$;
D—Phe—Gln—Trp—Ala—Val—Gly—His—Leu—Nle—$NH_2$;
D—Phe—Gln—Trp—Ala—Val—D—Ala—His—Leu—Nle—$NH_2$;
D—Phe—Gln—Trp—Ala—Val—Gly—His—Phe—Nle—$NH_2$;
D—Phe—Gln—Trp—Ala—Val—D—Ala—His—Phe—Nle—$NH_2$;
Ac—His—Trp—Ala—Val—D—Ala—His—Leu—Leu—$NH_2$;

cyclo—D—Phe—Gln—Trp—Ala—Val—Gly—His—Leu—Leu;

D—Cys—Asn—Trp—Ala—Val—Gly—His—Leu—Cys—$NH_2$;

cyclo—His—Trp—Ala—Val—Gly—His—Leu—Met;

Cys—Trp—Ala—Val—Gly—His—Leu—Cys—$NH_2$;

cyclo—D—Phe—Gln—Trp—Ala—Val—Gly—His—Leu—Met;

cyclo—D—Phe—His—Trp—Ala—Val—Gly—His—Leu—Met;

and cyclo—Trp—Ala—Val—Gly—His—Leu—Met.

Preferably, the analog administered according to methods of the invention includes between seven and ten amino acid residues, inclusive, and is an analog of one of the following peptides terminating at the carboxy-terminus with a Met residue: (a) litorin; (b) the ten amino acid carboxy-terminal region of mammalian GRP; and (c) the ten amino acid carboxy-terminal region of amphibian bombesin; the analog is of the following formula (II):

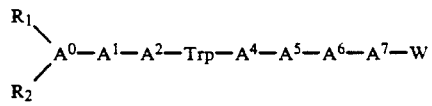

wherein $A^0$=pGlu, Gly, Nle, $\alpha$-aminobutyric acid, or the D-isomer of any of Ala, Val, Gln, Asn, Leu, Ile, Met, p-X-Phe (where X=F, Cl, Br, $NO_2$, OH, H or $CH_3$), Trp, Cys, or $\beta$-Nal, or is deleted;

$A^1$=the D or L-isomer of any of pGlu, Nle, $\alpha$-aminobutyric acid, or the D-isomer of any of Ala, Val, Gln, Asn, Leu, Ile, Met, p-X-Phe (where X=F, Cl, Br, $NO_2$, OH, H or $CH_3$), $F_5$-Phe, Trp, Cys, or $\beta$-Nal, or is deleted;

$A^2$=pGlu, Gly, Ala, Val, Gln, Asn, Leu, Ile, Met, p-X-Phe (where X=F, Cl, Br, $NO_2$, OH, H or ($CH_3$), Trp, Cys, $\beta$-Nal, His, 1-methyl-His, or 3-methyl-His;

$A^4$=Ala, Val Gln Asn Gly, Leu, Ile, Nle, $\alpha$-aminobutyric acid, Met, p-X-Phe (where X=F, Cl, Br, $NO_2$, OH, H or $CH_3$), Trp, Cys, or $\beta$-Nal;

$A^5$=Gln, Asn, Gly, Ala, Leu, Ile, Nle, $\alpha$-aminobutyric acid, Met, Val, p-X-Phe (where X=F, Cl, Br, OH, H or $CH_3$), Trp, Thr, or $\beta$-Nal;

$A^6$=Sar, Gly, or the D-isomer of any of Ala, N-methyl-Ala, Val, Gln, Asn, Leu, Ile, Met, p-X-Phe (where X=F, Cl, Br, $NO_2$, OH, H or $CH_3$), Trp, Cys, or $\beta$-Nal;

$A^7$=1-methyl-His, 3-methyl-His, or His;

provided that, if $A^0$ is present, $A^1$ cannot be pGlu; further provided that, if $A^0$ or $A^1$ is present, $A^2$ cannot be pGlu; further provided that, when $A^0$ is deleted and $A^1$ is pGlu, $R_1$ must be H and $R_2$ must be the portion of Glu that forms the imine ring in pGlu; and further provided that, W can be any one of the following:

(I):

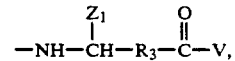

wherein $R_3$ is $CHR_{20}$—$(CH_2)_{n1}$ (where $R_{20}$ is either of H or OH; and n1 is either of 1 or 0), or is deleted, and $Z_1$ is the identifying group of any of the amino acids Gly, Ala, Val, Leu, Ile, Ser, Asp, Asn, Glu, Gln, p-X-Phe (where X=H, F, Cl, Br, $NO_2$, OH, or $CH_3$), $F_5$-Phe, Trp, Cys, Met, Pro, HyPro, cyclohexyl-Ala, or $\beta$-nal; and V is either $OR_4$, or

where $R_4$ is any of $C_{1-20}$ alkyl, $C_{3-20}$ alkenyl, $C_{3-20}$ alkinyl, phenyl, naphthyl, or $C_{7-10}$ phenylalkyl, and each $R_5$, and $R_6$, independently, is any of H, $C_{1-12}$ alkyl, $C_{7-10}$ phenylalkyl, lower acyl, or,

where $R_{22}$ is any of H, $C_{1-12}$ alkyl, $C_{7-10}$ phenylalkyl, or lower acyl; provided that, when one of $R_5$ or $R_6$ is $-NHR_{22}$, the other is H;

(II):

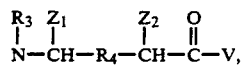

wherein $R_4$ is $CH_2-NH$, $CH_2-S$, $CH_2-O$, $CO-CH_2$, $CH_2-CO$, or $CH_2-CH_2$, and each $Z_1$ and $Z_2$, independently, is the identifying group of any one of the amino acids Gly, Ala, Val, Leu, Ile, Ser, Asp, Asn, Glu, Gln, $\beta$-Nal, p-X-Phe (where X=H, F, Cl, Br, $NO_2$, OH or $CH_3$), $F_5$-Phe, Trp, Cys, Met, Pro, HyPro, or cyclohexyl-Ala; and V is either $OR_5$ or

where each $R_3$, $R_5$, $R_6$, and $R_7$, independently, is H, lower alkyl, lower phenylalkyl, or lower naphthylalkyl;

(III):

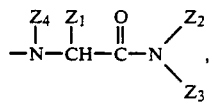

wherein $Z_1$ is the identifying group of any one of the amino acids Gly, Ala, Val, Leu, Ile, Ser, Asp, Asn, Glu, $\beta$-Nal, Gln, p-X-Phe (where X=H, F, Cl, Br, $NO_2$, OH or $CH_3$), $F_5$-Phe, Trp, Cys, Met, Pro, or HyPro; and each $Z_2$, $Z_3$, and $Z_4$, independently, is H, lower alkyl, lower phenylalkyl, or lower naphthylalkyl; or (IV):

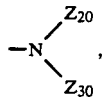

wherein each $Z_{20}$ and $Z_{30}$, independently, is H, lower alkyl, lower phenylalkyl, lower naphthylalkyl; further provided that, when either of $Z_{20}$ or $Z_{30}$ is other than H, $A^7$ is His, $A^6$ is Gly, $A^5$ is Val, $A^4$ is Ala, $A^2$ is His, and either of $R_1$ or $R_2$ is other than H, $A^1$ must be other than deleted; further provided that, for the formulas (I) through (IV), any asymmetric carbon atom can be R, S or a racemic mixture; and further provided that each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkinyl, phenyl, naphthyl, or $C_{7-10}$ phenylalkyl), or lower acyl, and $R_1$ and $R_2$ are bonded to the N-terminal amino acid of said peptide, and further provided that when one of $R_1$ or $R_2$ is $COE_1$, the other must be H, or a pharmaceutically acceptable salt thereof.

Analogs administered according to the invention may have one of the modifications given in generic formula (II) above; either a non-peptide bond instead of a peptide bond between an amino acid residue of the active site and an adjacent amino acid residue; or a synthetic amino acid, e.g. a statine, an AHPPA, or an ACHPA, a $\beta$-amino acid, or a $\gamma$-amino acid residue in place of two natural amino acid residues; or a deletion of the C-terminal amino acid residue, accompanied by the addition of a substituent on the actual C-terminal group and the presence of an N-terminal residue that is not the natural N-terminal amino acid residue of the peptides from which the analogs are derived. (Statine, AHPPA, and ACHPA have the chemical structures defined above. Where statine is used herein, AHPPA or ACHPA may also be used.)

By non-peptide bond is meant that the carbon atom participating in the bond between two residues is reduced from a carbonyl carbon to a methylene carbon, i.e., $CH_2-NH$; or, less preferably, that CO—NH is replaced with any of $CH_2-S$, $CH_2-O$, $CH_2-CH_2$, $CH_2-CO$, or $CO-CH_2$. (A detailed discussion of the chemistry of non-peptide bonds is given in Coy et al. (1988) Tetrahedron 44,3:835–841, hereby incorporated by reference, Tourwe (1985) Janssen Chim. Acta 3:3–15, 17–18, hereby incorporated by reference, and Spatola (1983) in Chemistry and Biochemistry of Amino Acids, Peptides, and Proteins, (B. Weinstein, ed.) M. Dekker, New York and Basel, pp. 267–357, hereby incorporated by reference.) The peptide bond reduction method which reduces a carbonyl carbon to a methylene carbon is described in Coy et al., U.S. patent application Ser. No. 879,348, hereby incorporated by reference.

One modification of the naturally occurring peptide to create an analog administered according to the invention is of the amino terminal end of the molecule, such as those described for the amino terminal positions in the generic formula (II) above; for example, the N-terminal amino acid residue, which is $A^0$ or, if $A^0$ is deleted, is $A^1$ or, if $A^0$ and $A^1$ are deleted, is $A^2$, may be an aromatic D-isomer, or may be an alkylated amino acid residue. (Where "D" is not designated as the configuration of an amino acid, L is intended.)

Preferably, the analog of generic formula II (above) is of the formula $A^0$=Gly, D-Phe, or is deleted;
$A^1$=p-Glu, D-Phe, D-Ala, D-$\beta$-Nal, D-Cpa, or D-Asn;
$A^2$=Gln, His, 1-methyl-His, or 3-methyl-His;
$A^4$=Ala;
$A^5$=Val;
$A^6$=Sar, Gly, D-Phe, or D-Ala;
$A^7$=His;
and, where W is (I) and $R_3$ is $CH_2$ or $CH_2-CH_2$, $Z_1$ is the identifying group of Leu or Phe, where W is (I) and $R_3$ is $CHOH-CH_2$, $Z_1$ is the identifying group of Leu, cyclohexyl-Ala, or Phe and each $R_5$ and $R_6$ is H; and where W is (I), V is $NHR_6$, and $R_6$ is $NH_2$; where W is (II) and $R_4$ is $CH_2-NH$ each $Z_1$ is the identifying group of Leu, or Phe, and $Z_2$ is the identifying group of Leu or Phe; where W is (III), $Z_1$ is the identifying group of any one of the amino acids Leu or p-X-Phe (where X=H, F, Cl, Br, $NO_2$, OH or $CH_3$); and each $Z_2$, $Z_3$ and $Z_4$, independently, is H, lower alkyl, lower phenylalkyl, or lower naphthylalkyl; and where W is (IV), each $Z_{20}$ and $Z_{30}$, is H; and each $R_1$ and $R_2$, independently, is H, lower alkyl, or lower acyl.

Preferred analogs include the following:

D-β-Nal-Gln-Trp-Ala-Val-Gly-His-LeuΨ[CH$_2$NH]-Phe-NH$_2$;

D-Phe-Gln-Trp-Ala-Val-Gly-His-Leu-ethylamide;

p-Glu-Gln-Trp-Ala-Val-Gly-His-statine-amide;

D-Cpa-Gln-Trp-Ala-Val-Gly-His-β-Leu-NH$_2$;

D-Cpa-Gln-Trp-Ala-Val-D-Ala-His-β-Leu-NH$_2$;

D-Cpa-Gln-Trp-Ala-Val-Gly-His-LeuΨ[CH$_2$NH]Phe-NH$_2$; and

D-Phe-Gln-Trp-Ala-Val-Gly-His-Leu-proplyamide;

Other preferred analogs include wherein W is (II), $R_4$ is CH$_2$—NH, and said carbon atom bonded to $Z_2$ is of said R configuration; for example, D-Phe-Gln-Trp-Ala-Val-Gly-His-LeuΨ[CH$_2$NH]-D-Phe-NH$_2$; and wherein W is (I), V is OR$_4$, and R$_4$ is any of $C_{1-20}$ alkyl, $C_{3-20}$ alkenyl, $C_{3-20}$ alkinyl, phenyl, naphthyl, or $C_{7-10}$ phenylalkyl, and $A^6$ is N-methyl-D-Ala or $A^1$ is D-F$_5$-Phe; for example, D-Phe-Gln-Trp-Ala-Val-N-methyl-D-Ala-His-Leu-methylester, and D-F$_5$-Phe-Glu-Trp-Ala-Val-D-Ala-His-Leu-methylester.

In the generic formulae (I and II) given above, when either of $R_1$ or $R_2$ is an aliphatic, aromatic, or lipophilic group, the in vivo activity can be long lasting, and delivery of the compounds of the invention to the target tissue can be facilitated.

Analogs administered according to the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluene sulfonic, trifluoroacetic, or pamoic acid, as well as polymeric acids such as tannic acid or carboxymethyl cellulose, and salts with inorganic acids such as the hydrohalic acids, e.g., hydrochloric acid, sulfuric acid or phosphoric acid.

Other features and advantages of the invention will be apparent from the following description of the preferred embodiments thereof, and from the claims.

DESCRIPTION OF THE PREFERRED EMBODIMENTS

We first briefly describe the drawings.

Drawings

FIG. 9 is a series of amino acid sequences of naturally occurring peptides of which peptides of the invention are analogs.

Figure 1:
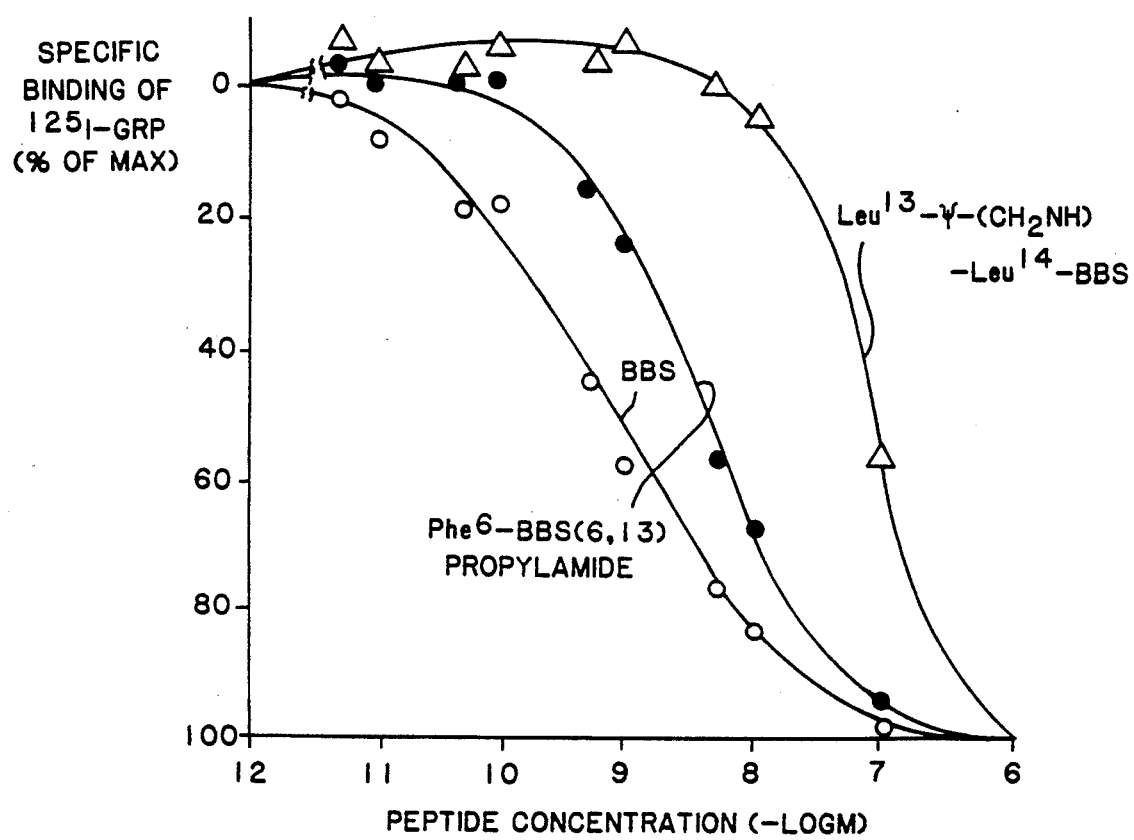
FIG. 1 is a graph showing binding of test peptides to mouse colon tumor cell membranes.

We now describe the structure, synthesis, and use of the preferred embodiments of the invention.

Structure

Peptides of the invention are derived from one of the sequences shown in FIG. 9, which represent the sequences, or portions thereof, of naturally-occurring peptides. Bombesin, neuromedin B, neuromedin C, litorin, and GRP analogs of the invention are described in Coy et al., U.S. patent application Ser. No. 502,438, filed Mar. 30, 1990, which is a continuation-in-part of U.S. patent application Ser. No. 397,169, filed Aug. 21, 1989, which is a continuation-in-part of U.S. patent application Ser. No. 376,555, filed Jul. 7, 1989, and U.S. patent application Ser. No. 394,727, filed Aug. 16, 1989, both of which are continuation-in-parts of U.S. patent application Ser. No. 317,941, filed Mar. 2, 1989, which is a continuation-in-part of U.S. patent application Ser. No. 282,328, filed Dec. 9, 1988, which in turn is a continuation-in-part of U.S. patent application Ser. No. 257,998, filed Oct. 14, 1988, which in turn is a continuation-in-part of U.S. patent application Ser. No. 248,771, filed Sep. 23, 1988, which in turn is a continuation-in-part of Coy et al., U.S. patent application Ser. No. 207,759, filed Jun. 16, 1988, which in turn is a continuation-in-part of Coy et al., U.S. patent application Ser. No. 204,171, filed Jun. 8, 1988, which in turn is a continuation-in-part of Coy et al., U.S. patent application Ser. No. 173,311, filed Mar. 25, 1988, which in turn is a continuation-in-part of Coy et al. U.S. patent application Ser. No. 100,571, filed Sep. 24, 1987; all of which are assigned to the same assignee and hereby incorporated by reference; or as described in Zachary et al., Proc. Nat. Aca. Sci. 82:7616, 1985; Heimbrook et al., "Synthetic Peptides: Approaches to Biological Problems", UCLA Symposium on Mol and Cell. Biol. New Series, Vol. 86, ed. Tam and Kaiser; Heinz-Erian et al., Am. J. Physiol. G439, 1986; Martinez et al., J. Med. Chem. 28:1874, 1985; Gargosky et al., Biochem. J. 247:427, 1987; Dubreuil et al., Drug Design and Delivery, Vol 2:49, Harwood Academic Publishers, GB, 1987; Heikkila et al., J. Biol. Chem. 262:16456, 1987; Caranikas et al., J. Med. Chem. 25:1313, 1982; Saeed et al., 1989, Peptides 10:597; Rosell et al., Trends in Pharmacological Sciences 3:211, 1982; Lundberg et al., Proc. Nat. Aca. Sci. 80:1120, 1983; Engberg et al., Nature 293:222, 1984; Mizrahi et al., Euro. J. Pharma. 82:101, 1982; Leander et al., Nature 294:467, 1981; Woll et al., Biochem. Biophys. Res. Comm. 155:359, 1988; Rivier et al., Biochem. 17:1766, 1978; Cuttitta et al., Cancer Surveys 4:707, 1985; Aumelas et al., Int. J. Peptide Res. 30:596, 1987; all of which are hereby incorporated by reference.

Synthesis of Analogs

The synthesis of the bombesin analog pGlu-Gln-Trp-Ala-Val-Gly-His-LeuΨ[CH$_2$NH]Leu-NH$_2$ follows. Other bombesin, litorin, GRP, or neuromedin B or C analogs can be prepared by making appropriate modifications of the following synthetic method.

The first step is the preparation of the intermediate pGlu-Gln-Trp-Ala-Val-Gly-His(benzyloxycarbonyl)-Leu Ψ[CH$_2$NH]Leu -benzhydrylamine resin, as follows.

Benzhydrylamine-polystyrene resin (Vega Biochemicals, Inc.) (0.97 g, 0.5 mmole) in the chloride ion form is placed in the reaction vessel of a Beckman 990B peptide synthesizer programmed to perform the following reaction cycle: (a) methylene chloride; (b) 33% trifluoroacetic acid (TFA) in methylene chloride (2 times for 1 and 25 min. each); (c) methylene chloride; (d) ethanol; (e)

methylene chloride; and (f) 10% triethylamine in chloroform.

The neutralized resin is stirred with alpha-t-butoxycarbonyl(Boc)-leucine and diisopropylcarbodiimide (1.5 mmole each) in methylene chloride for 1 hour, and the resulting amino acid resin is then cycled through steps (a) to (f) in the above wash program. Boc-leucine aldehyde (1.25 mmoles), prepared by the method of Fehrentz and Castro, Synthesis, p. 676 (1983), is dissolved in 5 ml of dry dimethylformamide (DMF) and added to the resin TFA salt suspension followed by the addition of 100 mg (2 mmoles) of sodium cyanoborohydride (Sasaki and Coy, Peptides 8:119-121 (1987); Coy et al., id.). After stirring for 1 hour, the resin mixture is found to be negative to ninhydrin reaction (1 min.), indicating complete derivatization of the free amino group.

The following amino acids (1.5 mmole) are then coupled successively in the presence diisopropylcarbodiimide (1.5 mmole), and the resulting amino acid resin is cycled through washing/deblocking steps (a) to (f) in the same procedure as above: Boc-His(benzyloxycarbonyl), Boc-Gly (coupled as a 6M excess of the p-nitrophenylester), Boc-Val, Boc-Ala, Boc-Trp, Boc-Gln (coupled as a 6M excess of the p-nitrophenylester), and pGlu. The completed resin is then washed with methanol and air dried.

The resin described above (1.6 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen, and free peptide is precipitated and washed with ether. The crude peptide is dissolved in a minimum volume of 2M acetic acid and eluted on a column (2.5×100 mm) of Sephadex G-25 (Pharmacia Fine Chemicals, Inc.). Fractions containing a major component by uv absorption and thin layer chromatography (TLC) are then pooled, evaporated to a small volume and applied to a column (2.5×50 cm) of octadecylsilane-silica (Whatman LRP-1, 15-20 μm mesh size).

The peptide is eluted with a linear gradient of 0-30% acetonitrile in 0.1% trifluoroacetic acid in water. Fractions are examined by TLC and analytical high performance liquid chromatography (HPLC) and pooled to give maximum purity. Repeated lyophilization of the solution from water gives 60 mg of the product as a white, fluffy powder.

The product is found to be homogeneous by HPLC and TLC. Amino acid analysis of an acid hydrolysate confirms the composition of the peptide. The presence of the Leu$\Psi$[CH$_2$—NH]Leu bond is demonstrated by fast atom bombardment mass spectrometry.

pGlu-Gln-Trp-Ala-Val-Gly-His-Phe$\Psi$[CH$_2$NH]Leu-NH$_2$, pGlu-Gln-Trp-Ala-Val-Gly-His-Leu$\Psi$[CH$_2$NH]Leu NH$_2$, pGlu-Gln-Arg-Leu-Gly-Asn-Gln-Trp-Ala-Val-Gly-D-Phe-Leu-Met-NH$_2$, pGlu-Gln-Arg-Leu-Gly-Asn-Gln-Trp-Ala-Val-Gly-D-Phe-Leu-Leu-NH$_2$, pGlu-Gln-Arg-Tyr-Gly-Asn-Gln-Trp-Ala-Val-Gly-D-Phe-Leu-Met-NH$_2$, or other peptides are prepared in similar yields in an analogous fashion by appropriately modifying the above procedure.

Solid phase synthesis of D-Phe[1], Leu[8]$\Psi$[CH$_2$NH]D-Phe[9]-litorin (D-Phe-Gln-Trp-Ala-Val-Gly-His-Leu$\Psi$[CH$_2$NH]-D-Phe-NH$_2$), was carried out as follows:

Boc-D-Phe-Gln-Trp-Ala-Val-Gly-His(tosyl)-Leu$\Psi$[CH$_2$NH]-D-Phe-benzhydrylamine resin was synthesized first.

Benzhydrylamine-polystyrene resin (Advanced ChemTech, Inc.) (1.25 g, 0.5 mmole) in the chloride ion form is placed in the reaction vessel of an Advanced ChemTech ACT 200 peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-D-phenylalanine and diisopropylcarbodiimide (1.5 mmole each) in methylene chloride for 1 h and the resulting amino acid resin is then cycled through steps (a) to (g) in the above wash program. The Boc group is then removed by TFA treatment. Boc-leucine aldehyde (1.25 mmoles), prepared by the method of Fehrentz and Castro (1), is dissolved in 5 ml of dry DMF and added to the resin TFA salt suspension followed by the addition of 100 mg (2 mmoles) of sodium cyanoborohydride (2,3). After stirring for 1 h, the resin mixture is found to be negative to ninhydrin reaction (1 min) indicating complete derivatization of the free amino group.

The following amino acids (1.5 mmole) are then coupled successively by the same procedure: Boc-His(benzyloxycarbonyl), Boc-Gly, Boc-Val, Boc-Ala, Boc-Trp, Boc-Gln (coupled in the presence of 1 equiv. hydroxybenzotriazole), Boc-D-Phe (coupled in the presence of 1 equiv. hydroxybenzotriazole). After drying, the peptide resin weighed 1.93 g.

The resin (1.93 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen and free peptide precipitated and washed with ether. The crude peptide is dissolved in a minimum volume of 2M acetic acid and eluted on a column (2.5×100 mm) of Sephadex G-25. Fractions containing a major component by uv absorption and thin layer chromatography are then pooled, evaporated to a small volume and applied to a column (2.5×50 cm) of Vydac octadecylsilane (10-15 uM). This is eluted with a linear gradient of 5-45% acetonitrile in 0.1% trifluoroacetic acid in water. Fractions are examined by thin layer chromatography and analytical high performance liquid chromatography and pooled to give maximum purity. Repeated lyophylization of the solution from water gives 120 mg of the product as a white, fluffy powder.

The product is found to be homogeneous by hplc and tlc. Amino acid analysis of an acid hydrolysate confirms the composition of the peptide. The presence of the Leu$\Psi$[CH$_2$NH] peptide bond is demonstrated by fast atom bombardment mass spectrometry.

The analog

D-Cpa-Gln-Trp-Ala-Val-Gly-His Leu-$\Psi$[CH$_2$NH]Phe-NH$_2$ may be synthesized in a similar manner by substituting D-Cpa (i.e., D-para-Cl-Phe) for D-Phe.

Solid phase synthesis of D-Phe[1]-Des-Met[9] litorin, D-Phe-Gln-Trp-Ala-Val-Gly-His-Leu-NH$_2$, was carried out as follows.

Step (1): Benzhydrylamine-polystyrene resin (Advanced ChemTech, Inc. (0.62 gm, 0.25 mmole) in the chloride ion form is placed in the reaction vessel of an ACT 200 peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-leucine and diisopropylcarbodiimide (1.5 mmole each) in methylene chloride for 1 hr and the resulting amino acid resin is then cycled through steps (a) to (g) in the above wash program. The following amino acids (1.5 mmole) are then coupled successively by the same procedure: Boc-His (benzyloxycarbonyl), Boc-Gly, Boc-Val, Boc-Ala, Boc-Trp, Boc-Gln (coupled as a 6M excess of the p-nitrophenylester, and pGlu (coupled in the presence of hydroxzybenzotriazole). After drying, the peptide resin weighed 0.92 g.

Step (2): The resin (0.92 g) is then mixed with anisole (5 ml), dithiothreitol (200 mg) and anhydrous hydrogen fluoride (35 ml) at 0° C. and stirred for 45 min. Excess hydrogen fluoride is evaporated rapidly under a stream of dry nitrogen and free peptide precipitated and washed with ether. The crude peptide is dissolved in a minimum volume of 2M acetic acid and eluted on a column (2.5×100 cm) of Sephadex G-25. Fractions containing a major component by UV absorption and thin layer chromatography are then pooled, evaporated to a small volume and applied to a column (2.5×50 cm) of Vydac octadecylsilane (10–15 microM). The column is eluted with a linear gradient of 0–30% acetonitrile in 0.1% trifluoroacetic acid in water. Fractions are examined by thin layer chromatography and pooled to give maximum purity. Repeated lyophilization of the solution from water gives a white, fluffy powder; this product is found to be homogeneous by hplc and tlc. Amino acid analysis of an acid hydrolysate confirms the composition of the peptide.

Synthesis of D-Nal-Gln-Trp-Ala-Val-Gly-His-Leu-$NH_2$ was accomplished using the same procedure as described above (0.62 g, 0.25 mmole of benzyhydrylamine resin in step (1), and 0.92 g in step (2)).

Synthesis of N-acetyl-D-Phe-Gln-Trp-Ala-Val-Gly-His-Leu-$NH_2$ was accomplished using the same procedure as that described above, using 0.62 g (0.25 mmole) of benzhydrylamine resin in step (1), and mixing 0.92 g of the resin with anisole in step(2), except that the final Boc group was removed and the resin acetylated with acetic anhydride in methylene chloride. The synthesis of $Sta^8$-Des-$Met^9$ litorin follows. A statine, AHPPA, or ACHPA residue can be substituted in place of any two amino acids of the analog, where the peptide contains only peptide bonds. For example, $sta^8$-des $Met^9$ litorin was prepared in an analagous fashion by first coupling statine to the resin and then proceeding with the addition of Boc-His(benzylocarbonyl). Statine or Boc-statine can be synthesized according to the method of Rich et al., 1978, J. Organic Chem. 43; 3624; and Rich et al., 1980, J. Med. Chem. 23: 27, and AHPPA and ACHPA can be synthesized according to the method of Hui et al., 1987, J. Med. Chem. 30: 1287; Schuda et al., 1988, J. Org. Chem. 53:873; and Rich et al., 1988, J. Org. Chem. 53:869.

Solid phase synthesis of the peptide BIM-26120, pGlu-Gln-Trp-Ala-Val-Gly-His-Sta-$NH_2$ was accomplished through the use of the following procedures in which alpha-t-butoxycarbonyl statine (prepared by the procedure of Rich et al., J. Org. Chem. 1978, 43, 3624) is first coupled to methylbenzhydrylamine-polystyrene resin. After acetylation, the intermediate p-Glu-Gln-Trp-Ala-Val-Gly-His(benzyloxycarbonyl)-Sta-methylbenzhydrylamine resin is prepared. The synthetic procedure used for this preparation follows in detail:

1. Incorporation of alpha-t-butoxycarbonyl statine on methylbenzhydrylamine resin.

Methylbenzhydrylamine-polystyrene resin (Vega Biochemicals, Inc.) (1.0 g, 0.73 mmol) in the chloride ion form is placed in the reaction vessel of a Vega 250C Coupler peptide synthesizer. The synthesizer was programmed to perform the following reactions: (a) methylene chloride; (b) 10% triethylamine in chloroform; (c) methylene chloride; and (d) dimethylformamide.

The neutralized resin is mixed for 18 hours with the preformed active ester made from alpha-t-butoxycarbonyl statine (1.46 mmol), diisopropyl carbodiimide (2 mmol), and hydroxybenzotriazole hydrate (1.46 mmol in dimethylformamide at 0° C. for one hour. The resulting amino acid resin is washed on the synthesizer with dimethylformamide and then methylene chloride. The resin mixture at this point was found by the Kaiser ninhydrin test (5 minutes) to have an 84% level of statine incorporation on the resin.

Acetylation was performed by mixing the amino-acid resin for 15 minutes with N-acetyl imidazole (5 mmol) in methylene chloride. Derivatization to the 94–99% level of the free amino groups of the resin was indicated by the Kaiser ninhydrin test (5 minutes). The Boc-statine-resin is then washed with methylene chloride.

2 Couplings of the Remaining Amino Acids.

The peptide synthesizer is programmed to perform the following reaction cycle: (a) methylene chloride; (b) 33% trifluoroacetic acid (TFA) in methylene chloride (2 times for 5 and 25 min. each); (c) methylene chloride; (d) isopropyl alcohol; (e) 10% triethylamine in chloroform; and (f) methylene chloride.

The following amino acids (2.19 mmol) are then coupled successively by diisopropyl carbodiimide (4 mmol) alone or diisopropyl carbodiimide (4 mmol) plus hydroxybenzotriazole hydrate (1.47 or 0.73 mmol) and the resulting peptide-resin is washed on the synthesizer with dimethylformamide and then methylene chloride, and then cycled through the washing and deblocking steps (a) to (f) in the procedure described above.

Boc-His (benzyloxycarbonyl) (coupled in the presence of 2 equivalents hydroxybenzotriazole); Boc-Gly; Boc-Val; Boc-Ala and Boc-Trp (coupled as the preformed hydroxybenzotriazole active esters made by reaction at 0° C. for one hour with 1 equivalent hydroxybenzotriazole hydrate); Boc-Gln and pGlu (also coupled as the preformed active esters of hydroxybenzotriazole made by reaction at 0° C. for one hour with 1 equivalent hydroxybenzotriazole hydrate). The completed peptide-resin is then washed with methanol and air dried.

The peptide-resin described above (1.60 g, 0.73 mmol) is mixed with anisole (2.5 mL), dithioerythritol (50 mg), and anhydrous hydrogen fluoride (30 ml) at 0° C. for one hour. Excess hydrogen fluoride is evaporated rapidly under a stream of dry nitrogen, and the free peptide is precipitated and washed with ether. The crude peptide is dissolved in 100 mL of 1M acetic acid and the solution is then evaporated under reduced pressure. The crude peptide is dissolved in a minimum volume of methanol/water 1/1 and triturated with 10 volumes of ethyl acetate.

The triturated peptide is applied to a column (9.4 mm I.D.×50 cm) of octadecylsilane-silica (Whatman Partisil 10 ODS-2M 9). The peptide is eluted with a linear gradient of 20–80% of 20/80 0.1% trifluoroacetic acid/acetonitrile in 0.1% trifluoroacetic acid in water. Fractions are examined by TLC and analytical high performance liquid chromatography (HPLC) and pooled to give maximum purity. Lyophilization of the solution from water gives 77 mg of the product as a white fluffy powder.

The synthesis of the bombesin agonist, BIM-26187, D-Phe-Gln-Trp-Ala-Val-Gly-His-Leu-Leu-NH$_2$ follows. Other bombesin or GRP agonists can be prepared by making appropriate modifications of the following synthetic method.

1) Incorporation of alpha-t-butoxycarbonyl (BOC)-leucine on 4-methyl benzhydrylamine.

4-methyl benzhydrylamine-polystyrene resin (Bachem, Inc.) (0.72 meg/g) in the chloride ion form is placed in the reaction vessel of an ACT200 peptide synthesizer (Advanced Chem Tech, Inc.) programmed to perform the following reaction cycle: (a) methylene chloride; (b) 10% triethylamine in chloroform; (c) methylene chloride; and (d) dimethylformide.

The neutralized resin is mixed with alpha-t-butoxycarbonyl (BOC)-leucine and diisopropylcarbodiimide (3 molar eg each) in methylene chlrodie for 1 hour. The resulting amino acid resin is washed on the synthesizer with dimethylformamide and treated with 5% acetic anhydride in dimethylformamide for 5 min. Then it is washed with dimethylformamide and methylene chloride.

2) Couplings of the remaining amino acids.

The peptide synthesizer is programmed to
perform the following reaction cycle: (a) methylene chloride; (b) 33% trifluoroacetic acid (TFA) in methylene chloride (2 times for 5 and 25 min. each); (c) methylene chloride; (d) isopropyl alcohol; (e) 10% triethylamine in chloroform; and (f) methylene chloride.

The following amino acids (3 molar eg.) are then coupled successively by the same procedure: BOC-Leu, BOC-His (tosyl), BOC-Gly, BOC-Val, BOC-Ala, BOC-Trp, BOC-Gln (coupled in the presence of 1 eg. hydroxybenzotriazole), BOC-D-Phe (coupled in the presence of 1 eg. hydroxybenzotriazole). The completed resin is then washed with methanol and air dried.

The peptide resin described above (1.41 g) is mixed with anisole (5 ml), dithioerythreitol (50 mg), and anhydrous hydrogen fluoride (25 ml) at 0° C. for one hour. Excess hydrogen fluoride is evaporated rapidly under a stream of dry nitrogen, and the residue is washed in ether. Crude peptide is dissolved in 100 ml of 4M acetic acid and the solution is then evaporated under reduced pressure. The crude peptide is dissolved in minimum volume of methanol/water and triturated with ethyl acetate. The triturated peptide is applied to a column (9.4mm I.D.×50 cm) of octadecylcilane-silica (Whatman Partisil 10 ODS - 2M9). The peptide is eluted with a linear gradient of 20–80% of 50/50 0.1% TFA/Acetronitrile i 0.1% TFA in water. Fractions are examined by analytical high performance liquid chromatography and appropriate fractions are evaporated to a small volume, which is further lyophilized, gives 65 mg of the product as a colorless powder.

Other compounds including D-Cpa$^1$, β-leu$^8$, desMet$^9$ Litorin, or compounds containing, e.g., CHx-Ala$^8$ or Nle$^9$, can be prepared as above; a statine, AHPPA, ACHPA, β-amino acid, or γ-amino acid residue is added in the same way as is a natural α-amino acid residue, by coupling as a Boc derivative.

Peptides modified at their C-terminal end can be prepared by appropriate modifications of the procedure described above. For example, O-methyl ester derivatives can be synthesized as described in Camble et al., "ICI 216140 A Potent In Vivo Antagonist Analogue of Bombesin/Gastrin Releasing Peptide Derived From the C-Terminal Sequence Lacking the Final Methionine Residue", Life Science, Oct.-Nov. 1989, hereby incorporated by reference; e.g., Camble et al. (id.) describe the synthesis of an analog of Bombesin having a trimethylacetyl-modified N-terminus and a methyl-ester modified C-terminus. This analog, $(CH_3)C-CO$-His-Trp-Ala-Val-D-Ala-His-Leu-$OCH_3$, can be synthesized by solid phase methods, as described above. The N-terminal trimethylacetyl modification can be obtained by reaction of the corresponding anhydrides with the peptide. The C-terminal methyl ester modification can be obtained by treating the peptide resin with methanol and triethylamine.

Peptides of the invention may be cyclized by formation of disulfide bridges if there are two cysteine residues present in the peptide, or according to the following procedure if in the absence of a cys-cys disulfide linkage.

Crude peptide acid obtained from peptide-resin ester by HF cleavage is dissolved in DMF (0.1%–1% concentration), treaed with condensing agent (e.g., BOP reagent, DEPC, DPPA, or any other condensing agent) followed by base (e.g., triethylamine, diisopropylethylamine) at room temperature for 1-3 days. Solvent is removed in vacuum to dryness. The residue is purified by HPLC, according to conventional procedures. The cyclization of, for example, cyclo[D Phe$^1$, Leu$^8$, Leu$^9$]-Litorin, in which D-Phe$^1$ is covalently linked to Leu$^9$, is accomplished according to the above procedure using Benzotriazol-1-yloxytris(dimethylamine)phosphonium hexafluorophosphate a the BOP reagent, diethylcyanophosphonate as the DEPC reagent, and diphenylphosphoryalazide as the DPPA reagent.

Tumor Test Systems

The analogs were tested in at least one of three types of tissues which included six tumor test systems: (1) a human colon tumor test system, (2) a human prostate tumor test system, (3) a rat prostate tumor test system, (4) a human breast tumor test system, and (5) and (6) two rat mammary tumor test systems, one of which is estrogen-sensitive and the other estrogen-insensitive.

The human colon tumor used for testing was the CX-5 tumor, which was surgically removed from a 50 year old human male and carried as an implant in athymic nude mice. The patient had been untreated prior to surgical removal of the tissue specimen. The tumor was found to be responsive to cisplatin and Adriamycin, but poorly responsive to cyclophosphamide. CX-5 was a moderately well-differentiated, mucin secreting adenocarcinoma. The tumor is arranged in acini lined by one or more layers of lining cells which have round to oval visicular nuclei containing prominent nucleoli. There are frequent mitoses, and the cells have eosinophilic cytoplasm. The acini contain abundant amounts of mucin.

A human prostate tumor, H-1579, was also isolated as a surgical specimen. Both the H-1579 prostate tumor and the CX-5 colon tumor were tested in the 11-day subrenal capsule assay (SRCA) (Bogden et al., 1978, Proc. Symp. Use of Athymic (Nude) Mice in Cancer Research, p. 231, Ed. Houchens and Ovejera, Gustav Fischer, N.Y.; Bogden et al., 1982, The Nude Mouse in Experimental and Clinical Research, 2:367, Ed. Fogh and Giovanella, Academic Press, NY; Goldin et al., 1981, Euro. J. of Cancer 17:129; Venditti, 1981, Sem. Oncol. 8:349; all of which are hereby incorporated by reference). The Rat Dunning prostate tumor R-3327-H was tested in a 19-day subrenal capsule assay. The 13762NF and MT/W9A-R rat mammary tumors were tested in 7 and 11 day subrenal capsule assays, respectively, and the MCF-7 human breast tumor was tested in a 15-day subrenal capsule assay using estrogen pelleted animals.

The human breast tumor cell line MCF-7 was initially explanted to in vitro culture from the pleural effusion of a breast adenocarcinoma in a 69-year old Caucasian female who had been treated with radiation and hormone therapy. The tumor was then established in in vivo passage in athymic nude mice. MCF-7 is estrogen-dependent, i.e., it requires the addition of exogenous estrogen for progressive growth. It is routinely passaged in mice either treated with i.m. injections of $17\beta$-estradiol or implanted S.C. with estrogen pellets of 3 weeks duration. Patel et al. (1990, Cancer Res. 50:235) have shown that both bombesin and GRP induce an increase in phospholipid hydrolysis and $CA^{2+}$ efflux in this tumor system.

The rat mammary adenocarcinoma 13762NF was originally induced in a Fischer 344 strain female (i.e., treated with dimethylbenzanthracene (DMBA)). 13762NF is not estrogen dependent, and is well established in serial transplantation; compared to MCF-7 it is relatively fast growing. This tumor has been reported to contain bombesin-like immunoreactivity (Guadino et al., 1986, Ann. NY Acad. Sci. 464:450). However, bombesin receptors have not been detected. It is routinely passaged in female Fischer 344 strain rats.

The MT/W9A-R rat mammary adenocarcinoma is an estrogen-independent subline of the estrogen-dependent MT/W9A (KIM) rat mammary adenocarcinoma. The tumor line was derived from an MT/W9A(-KIM) tumor that had escaped castration effects. It is routinely passaged in ovariectomized Wistar/Furth female rats.

Subrenal Capsule Assay

Briefly, tumors, 6–15 mm in diameter, were removed from the athymic mice and immediately placed in RPMI medium (Gibco, Grand Island, N.Y.) at room temperature. In the case of the larger tumors (over 10 mm in diameter), where the central parts frequently contained necrotic tissue, viable tissue was dissected out and placed in a separate Petri dish. The tissue pieces, while immersed in the medium, were cut with scalpels into cubes of approximately 1 mm.

Nude mice were anesthesized by i.p. injection of chloral hydrate (0.35–0.45 ml of a 0.22 M solution). A shallow incision was made in the left flank and the kidney was exteriorized. A shallow incision about 3 mm long was made on the convex side of the kidney near the caudal pole. The tissue fragment was implanted (one xenograft in each animal) below the transparent capsule by means of a small trochar (1.2 mm bore). Immediately after implantation, the tumor size was measured as described below. The abdominal wall was closed with sutures and the skin with clamps. To avoid hypothermia after the anesthesia, the animals were kept under an infra-red lamp for about 1 h, and then randomized into cages.

After 11 or 19 days the animals were killed, the kidney was removed and the size of the tumor was measured in situ with a stereoscopic microscope, fitted with an ocular micrometer, calibrated in ocular units (OMU) (10 OMU = 1 mm). Two perpendicular diameters were measured, and the difference in mean tumor diameter over the 11 or 19-day periods were calculated.

For the breast tumor studies, thirty-two athymic nude female mice were maintained on sterile water and food ad libitum in a biocontainment facility for 15 days for acclimatization. On day minus one, 24 mice (3 groups of 8 per group) were implanted s.c. with estrogen pellets having a 21-day duration potential. A control group of 8 mice were not pelleted. Twenty-four hours later (day 0), all animals were implanted sub-renal capsule with 1 $mm^3$ grafts of the MCF-7 tumor. Each fragment was carefully measured immediately after being positioned under the kidney capsule. The initial size of the tumor was thus measured in situ with a stereoscopic microscope fitted with an ocular micrometer calibrated in ocular micrometer units (omu), 10 omu = 1 mm. Two perpendicular diameters were measured, and the difference in mean diameter over the 15-day assay period was calculated.

Estrogen pelleted animals were randomized into control and test groups, 4 mice to a cage. Treatment was initiated on day 1, i.e., 24 hours post implantation according to the regimen shown in Table 1. Treatments were b.i.d. except for the weekend when the total daily dose was administered in one treatment.

As an antitumor screening procedure, all breast tumors, both human and rat, were tested as xenografts in athymic nude females. Assays varied in duration reflecting the individual tumor growth rates. The subrenal capsule assay (SCRA) method used for testing has been published in detail (Bogden et al., In: Proc. Symp. Use of Athymic (Nude) Mice in Cancer Research, p. 231, Ed. Houchens and Ovejera, Gustav Fisher: New York 1978) and is described above. However, except for the implantation of estrogen pellets, which was only necessary for the MCF-7 breast tumor, the SRCA methodology described for testing MCF-7 was essentially the same as the used for testing 13762NF (7 days), and MT/W9A R (11 days) (see above).

The subcutaneous tumor assay was used to confirm SRCA's results. Tumor xenografts are implanted s.c. rather than sub renal capsule on day 0. Tumors are measured with sensitive Vernier calipers and tumor size (length+width/2)mm or tumor weight (length-$\times$width$^2$/2) mg calculated. Tumors are implanted s.c. in the right flank and test compounds injected s.c. in the left flank. In addition to tumor size or weight, this assay system permits the parameter of "lag time", i.e., the effect of early treatment on the growth potential of tumors to reach a certain size.

Results of Colon and Prostatic Cancer Tests

The Bombesin analog BIM-26147 (D-Phe-Gln-Trp-Ala-Val-Gly-His-Leu-propylamide) was tested for the ability to inhibit colon tumor growth using the mouse colon cancer tumor MC-26. These results are presented in Table 1 and FIGS. 1 and 2. The Bombesin analogs BIM-26159 and BIM-26187, D-Cpa-Gln-Trp-Ala-Val-Gly-His-Leu$\Psi$[CH$_2$NH]Phe-NH$_2$ and D-Phe-Gln-Trp-Ala-Val-Gly-His-Leu-Leu-NH$_2$, respectively, were tested for the ability to inhibit colon tumor growth using the 11-day SRCA and the human colon tumor CX-5. The results are presented in Table 2 and FIG. 3, Table 3 and FIG. 4, and FIG. 5.

The bombesin analog BIM-26147 was tested for the ability to inhibit growth of the mouse colon tumor MC 26. The results demonstrate that mouse colon cancer cells have bombesin receptors and that BIM-26147 binds to these receptors.

Figure 2:
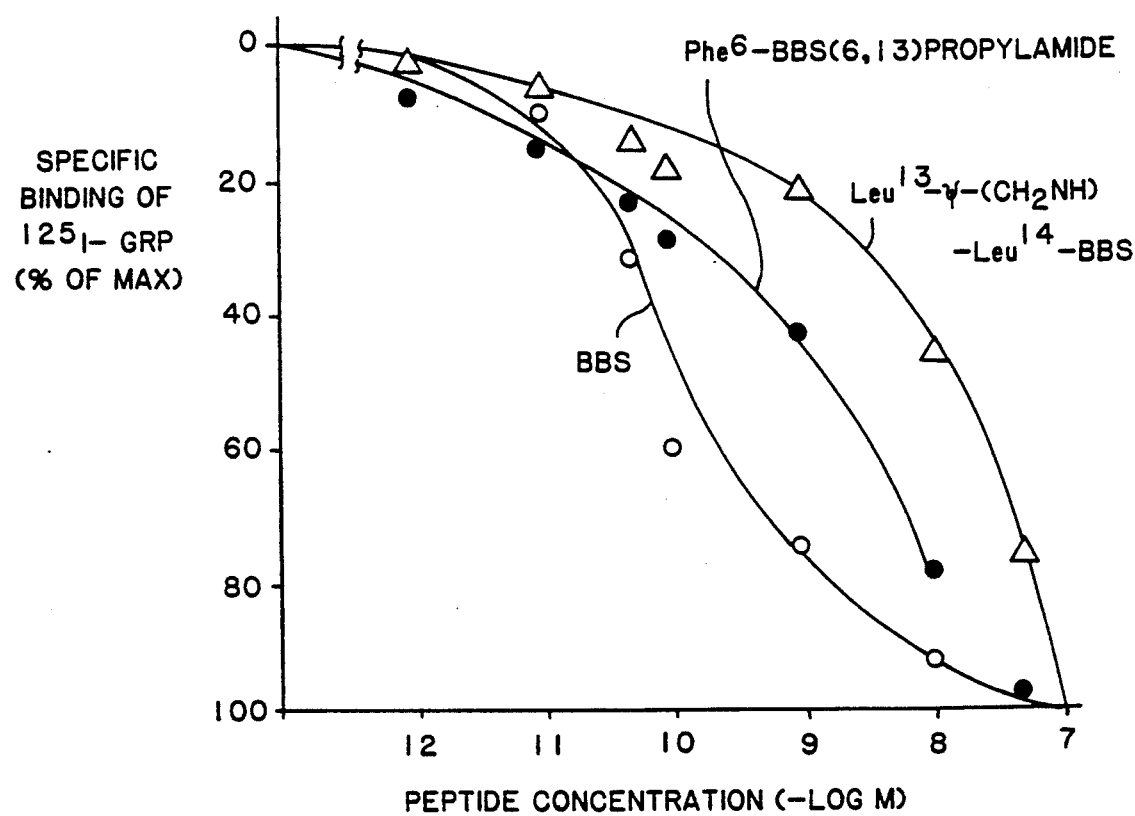
FIG. 2 is a graph showing binding of test peptides to mouse mucosal cell membranes.

FIG. 1 shows results of log-dose inhibition of specific binding of $^{125}$I-GRP to MC-26 tumor membranes by increasing concentrations of the three test peptides, bombesin (BBS), BIM-26147, or Leu$^{13}\Psi$[CH$_2$NH-]Leu$^{14}$bombesin (BIM-26028) FIG. 2 shows results of log-dose inhibition of specific binding of $^{125}$I-GRP to normal mouse colon mucosal membranes by increasing concentrations of the three test peptides. For both FIGS. 1 and 2, aliquots of tumor membranes (150 μg protein) were incubated with 20 pM of $^{125}$I-GRP in the presence of increasing concentrations of peptides, and the displacement of specifically bound $^{125}$I-GRP to MC-26 tumor membranes by increasing concentrations of peptides is presented as a percent of maximum specific binding of $^{125}$I-GRP. Each data point is the mean of two observations within an experiment, and represents two experiments. Table 1 presents the IC$_{50}$ for $^{125}$I-GRP binding to mouse colon cancer (MC-26) cells and normal colon mucosal cells in the presence of bombesin receptor antagonists. The data in Table 1 was calculated from FIGS. 1 and 2. The fold difference is relative to bombesin (BBS) values.

Figure 3:
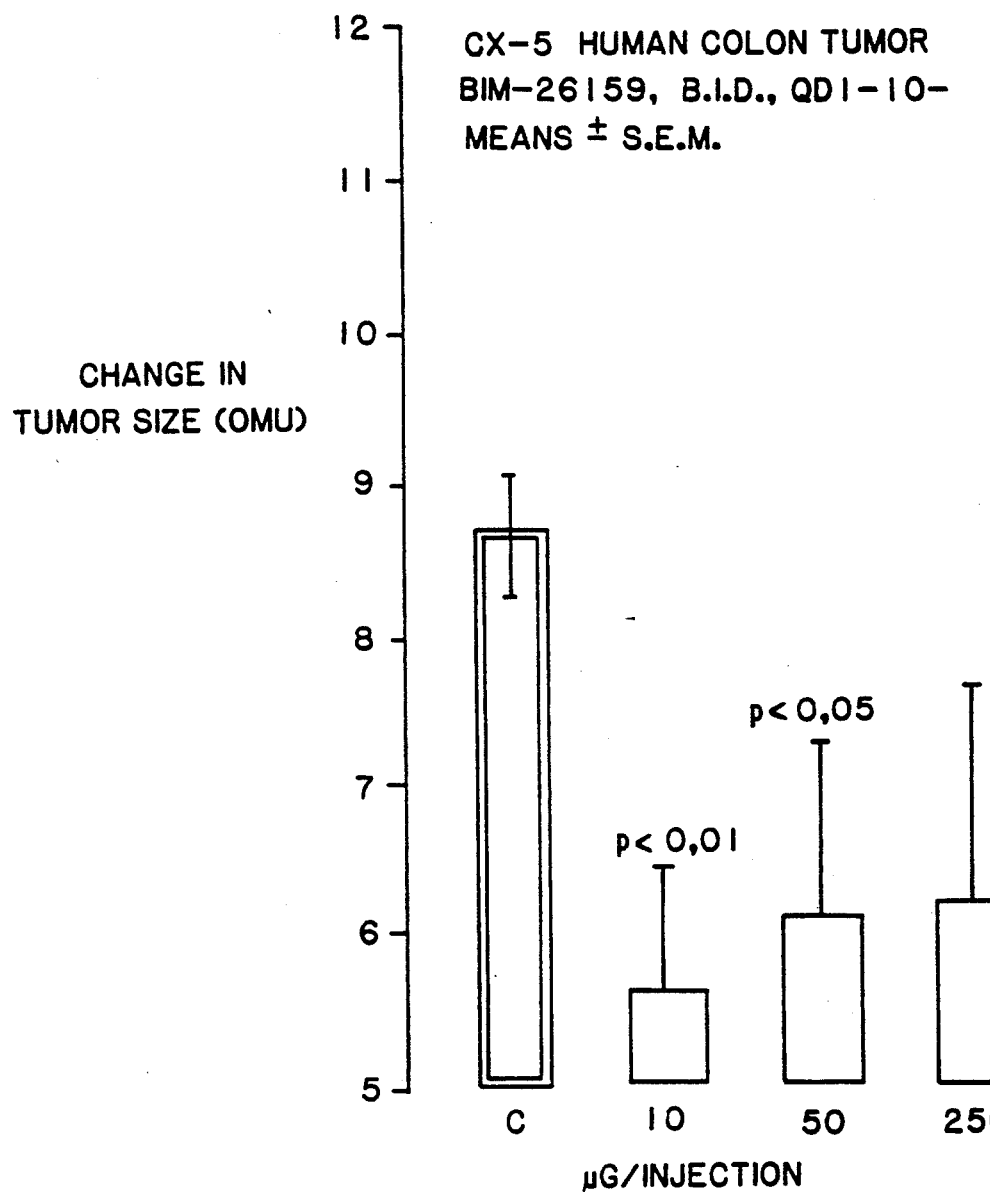
FIGS. 3 and 4 are graphs illustrating the growth inhibitory effect of different dosages of the bombesin analog designated BIM-26159 on the CX-5 human colon tumor.
Figure 4:
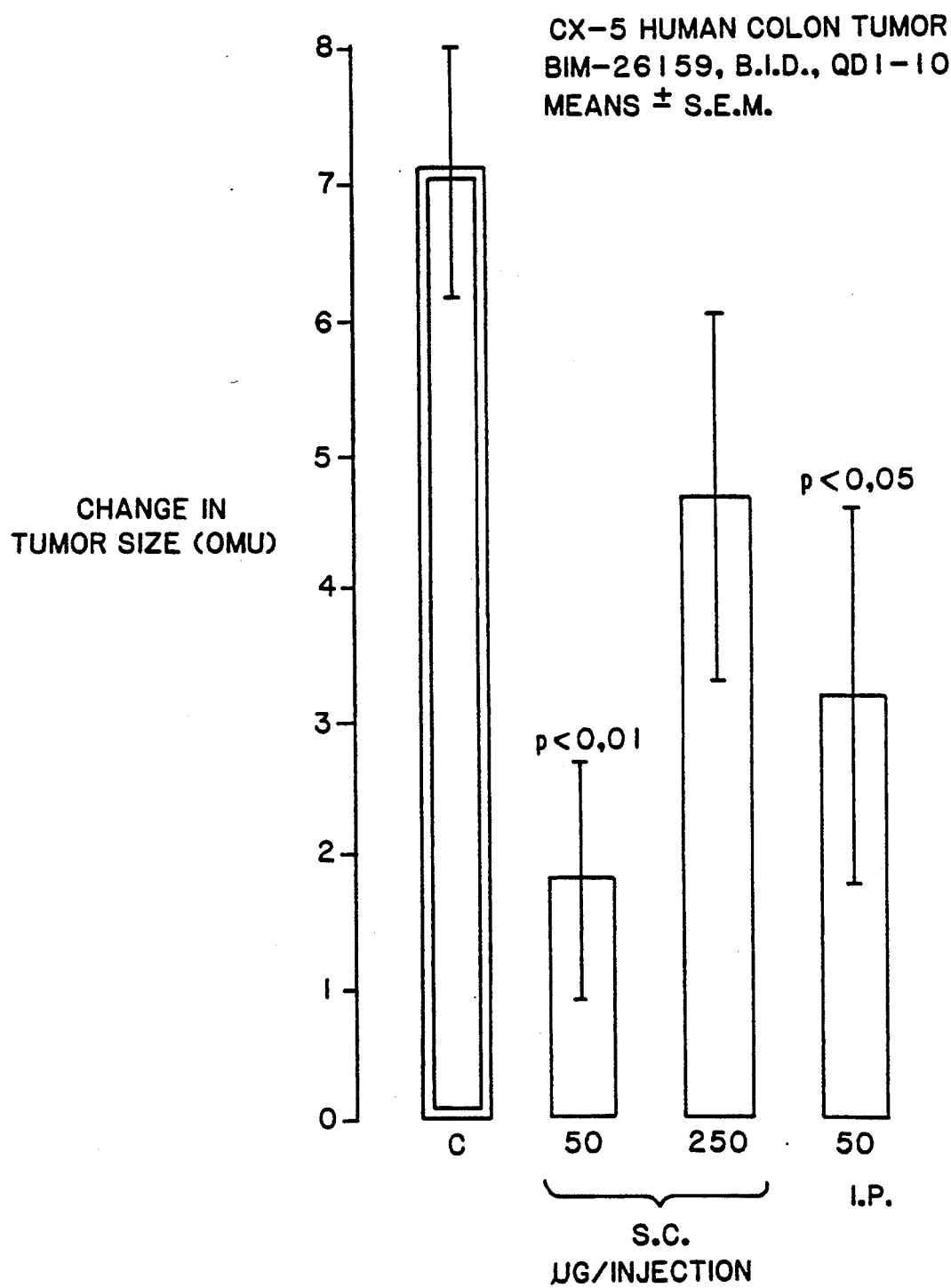

Table 2 and FIG. 3 shows that intraperitoneal (i.p.) administration of the two lowest dosages (10 μg and 50 μg) of the analog BIM-26159 significantly inhibited growth of the tumor. The high dose (250 μg) also inhibited tumor growth. Table 3 and FIG. 4 shows essentially the same results for this analog, and also that s.c. administration of the analog resulted in greater inhibition of tumor growth. There was no measurable effect on body weight as a result of treatment in either test.

Figure 5:
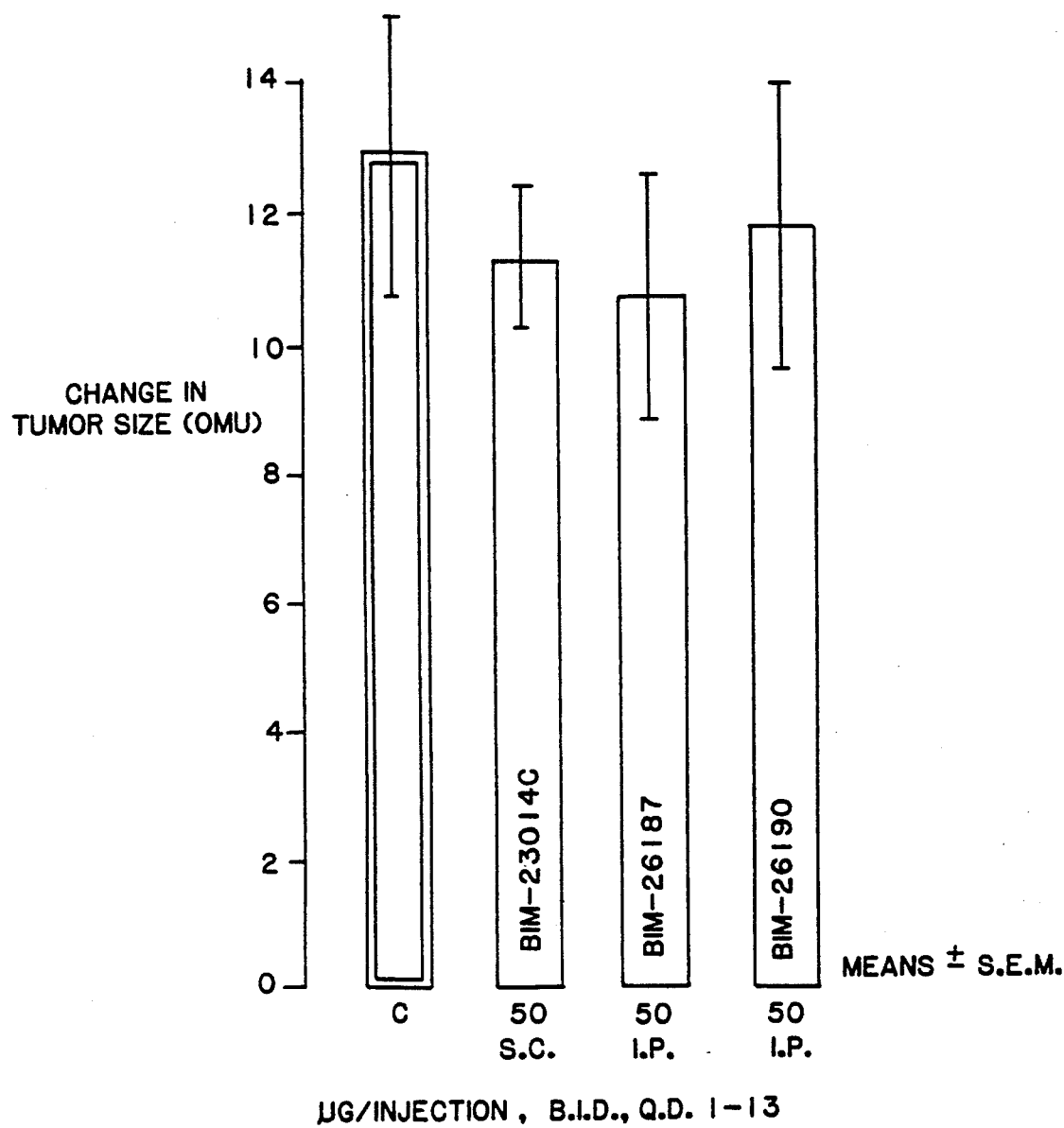
FIG. 5 is a graph illustrating the growth inhibitory effect of the bombesin analog BIM-26187 on the CX-5 human colon tumor.

FIG. 5 shows the effect of the analogs BIM-26187 and BIM-26190 on the growth of the CX-5 human colon tumor. At a dosage of 50 μg/injection, i.p., b.i.d., q.d. 1-13, the analog BIM-26187 resulted in a significant reduction in the size of the tumor as compared to analog BIM-26190 and the somatostatin peptide BIM-230146.

Figure 6:
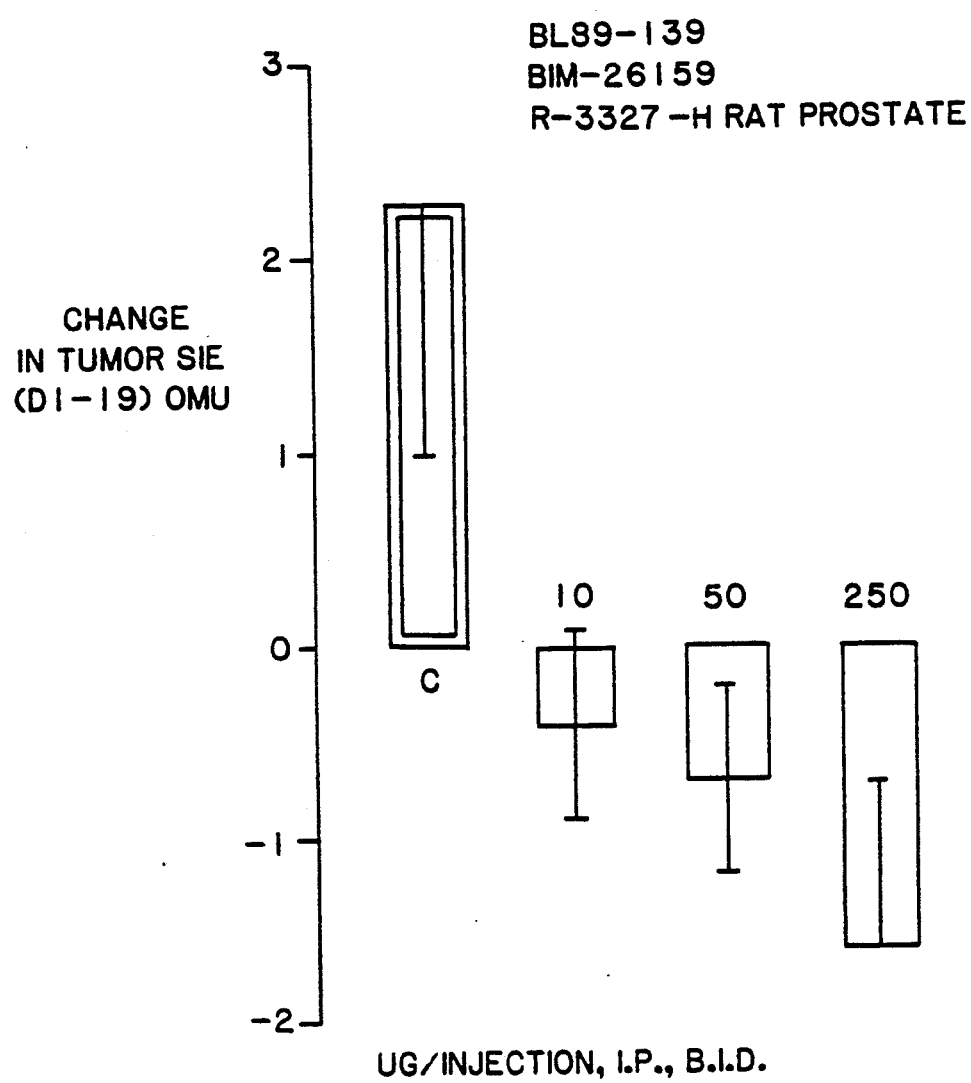
FIG. 6 is a graph illustrating the growth inhibitory effect of different dosages of the bombesin analog BIM-26159 on the R-3327-H rat prostate tumor.
Figure 7:
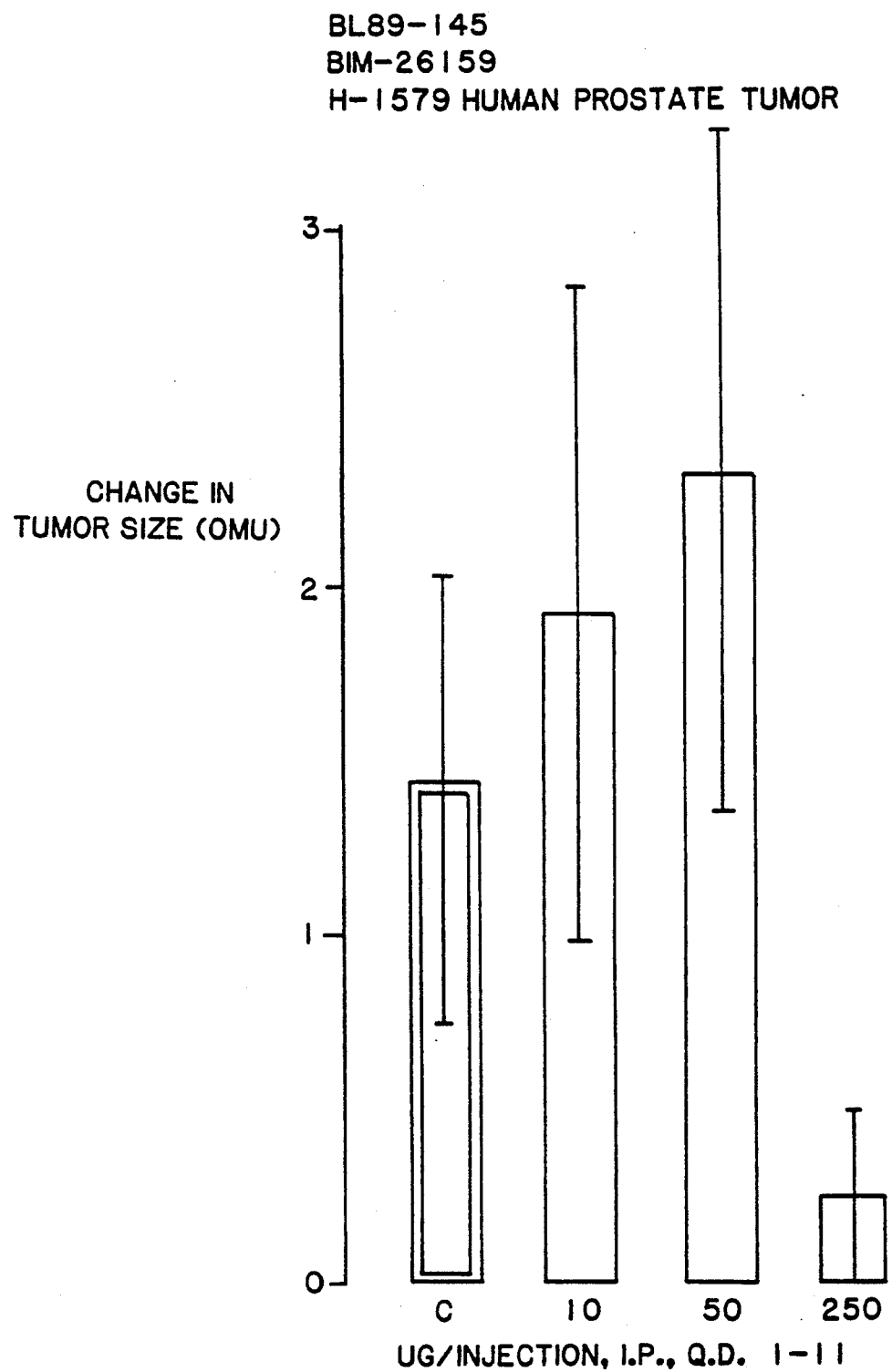
FIG. 7 is a graph illustrating the growth inhibitory effect of different dosages of the bombesin analog BIM-26159 on the H-1579 human prostate tumor.

The bombesin analog BIM 26159 was also tested for the ability to inhibit growth of the human and the rat prostatic tumors, R-3327-H (FIG. 6) and H-1579 (FIG. 7), respectively. The results, shown in FIGS. 6 and 7, demonstrate a reduction in tumor size. In the case of the R-3327-H rat prostatic tumor, BIM-26159 not only drastically reduced the size of the tumor, but resulted in shrinkage of the tumor to smaller than its original size (FIG. 6); this effect was dosage dependent. The H-1579 human prostatic tumor also responded dramatically to the B M-26159 analog at the highest dose tested, 250 μg/injection, i.p., q.d. 1-11 (FIG. 7).

Results of Breast Tumor Tests

Figure 8:
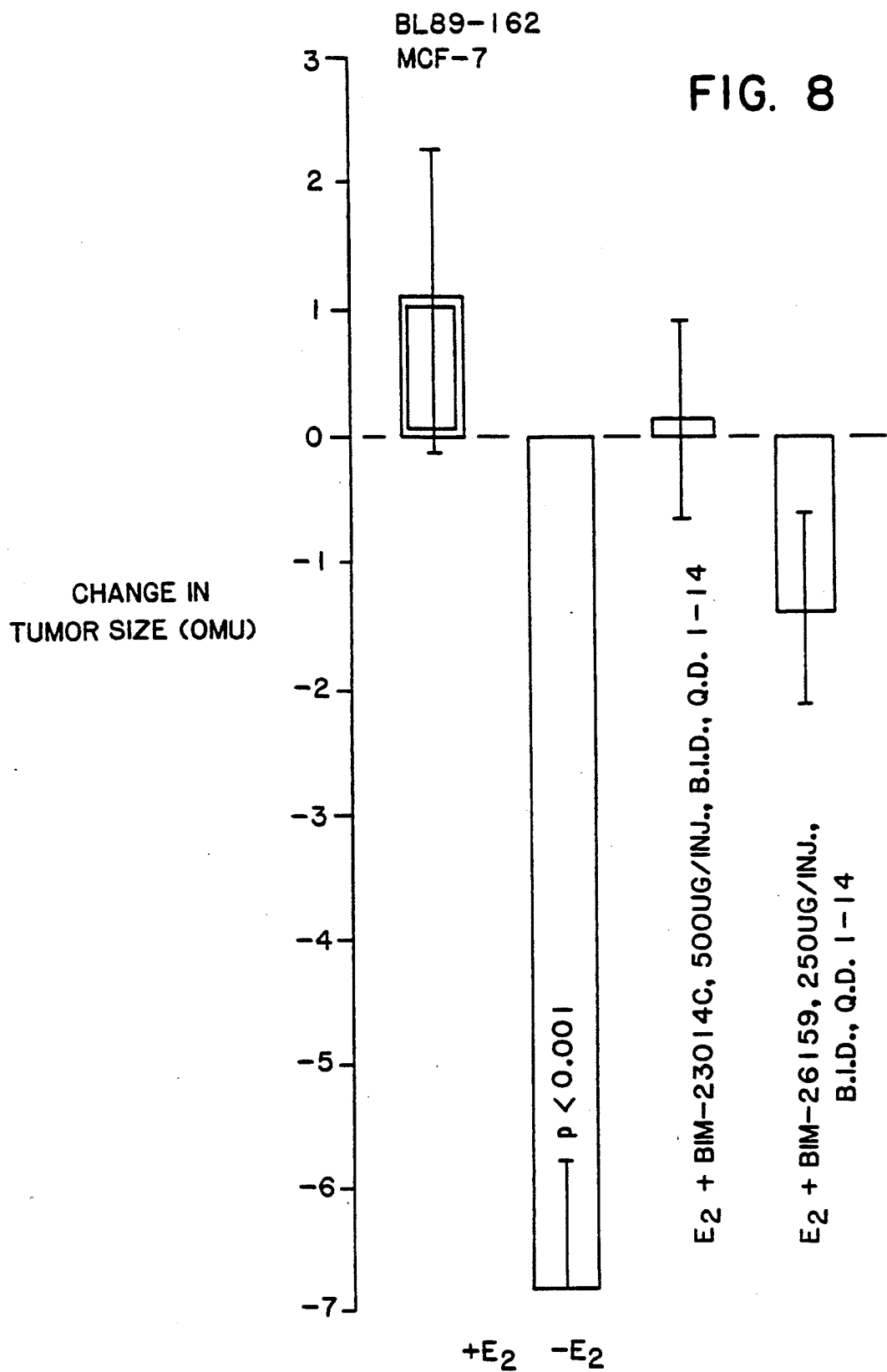
FIG. 8 is a bar graph of change in human breast tumor growth after treatment with BIM-26159.

Two bombesin analogs, BIM-26159 and BIM-26147, were screened in vivo for antitumor activity on the human breast tumor MCF-7 and the two rat mammary tumors, 13762NF and MT/W9A-R. Response of the MCF-7 human breast tumor to the bombesin analog BIM-26159 is summarized in Table 4 and illustrated in FIG. 8. The test system was a 15-day SRCA using estrogen pellet implanted animals. MCF-7 implanted in pelletized athymic nudes is slow growing whether implanted s.c. or under the renal capsule. The SRCA permits an initial tumor size measurement for calculating a more accurate change in tumor size. Estrogen pellet-implanted, saline vehicle-treated control tumors showed an increase in size. Xenografts implanted in unpelleted control animals (Gp.2) showed a marked decrease in size. Treatment of estrogen pelleted animals with BIM-26159 also induced a decrease in tumor size (Gp.3). Group 4 animals were treated with a somatostatin analog BIM-23014C as a positive control. Previous studies had shown that BIM-23014C was capable of inhibiting growth of the MCF-7 breast tumor. Therefore, in the current assay, BIM-23014C was used to confirm the responsiveness of MCF-7 xenografts to an anti-mitogen when implanted in estrogen pelleted hosts.

Two bombesin analogs were tested against the 13672NF tumor system, BIM-26159 and BIM-26147. Response of the 13762NF mammary tumor to BIM-26159 in a 7-day SRCA is summarized in Table 5. The high dose induced an inhibitory effect (83% T/C), the middle dose was inactive (96% T/C), and the lowest dose exhibited a slight stimulatory effect (128% T/C). Note that the brevity of the assay (7-days) was necessitated because of the tumor's rapid growth rate.

To provide a more stringent test system, the bombesin analog BIM-26147 was tested against the 13762NF breast tumor in the longer term subcutaneous tumor assay. The tumor inhibitory effects are summarized for two time points; on day 9 in Table 6 and on day 15 in Table 7. Treatment of 13762NF with BIM-26147 for 8 days inhibited growth of subcutaneously implanted tumors at the high dose (61% T/C). At the low dose (50 μg/injection), BIM-26147 exhibited no tumor growth inhibitory effects when administered s.c. on the side opposite of the tumor, but the same dose was growth inhibitory when administered as a s.c. infusion around the tumor. The growth inhibitory effects of BIM-26147, or lack thereof, was also reflected in the lag time for the various groups (Table 6). Although tumors in all groups were markedly enlarged by day 14, the growth inhibitory effects of BIM-26147 at the high dose are still in evidence (Table 7).

The estrogen resistant rat mammary adenocarcinoma MT/W9A-R was significantly inhibited (p<0.05) by the bombesin analog BIM-26159 in an 11-day SRCA (Table 8). The inhibitory effect was induced by the middle dose (150 μg). Both the low dose (10 μg) and the high dose (250 μg) were inactive, producing an inverted bell-shaped dose response.

Tumor responses are summarized in Table 9. The MCF-7 and MT/W9A-R tumors were inhibited by BIM-26159 and the 13762NF tumor, reported to contain bombesin-like immunoreactivity (Guadino et al., supra), was inhibited by both bombesin analogs.

Mechanism of Action

Analogs of the invention may prevent or inhibit the growth of cancer cells by acting as agonists, partial agonists, or antagonists; i.e., the analog may mimic or enhance the effect of binding of the natural peptide to the receptor or may competitively inhibit its binding. None of the breast tumors tested in these studies had detectable bombesin receptors, suggesting that the growth inhibition or stimulation observed with these tumors was inducible by intracellular mechanisms that were not bombesin receptor dependent. One possible mechanism of analog inhibition of growth of cancer cells is suggested in Bunn et al. (1990, Proc. Nat. Aca. Sci. 87:2162), in which calcium ion flux was measured in CHO cells after administration of one or more neuropeptides. Bunn et al. observe that, after the return of calcium concentration to resting values and upon administration of a second dose of an identical peptide, no calcium flux resulted from the second dose. However, when the second dose was administered using a different peptide, a new calcium flux occurred. Thus different peptides may trigger different calcium flux pathways. The results of Bunn et al. show that desensitization to the neuropeptide may occur both in cancerous and normal tissue, thus suggesting that an agonist or antagonist may suppress growth in a tumor cell by a similar mechanism.

Use

Methods of the invention are useful for treating colon, prostatic, breast, pancreatic, and lung cancer. Methods of the invention involve the administration of the analogs disclosed above to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes, or rectally (e.g., by suppository or enema). The analogs can be administered to a human patient in a dosage of 0.25 µg/kg/day to 5 mg/kg/day.

Other embodiments are within the following claims.

TABLE 1

DETERMINATION OF $IC_{50}$ FOR $^{125}I$-GRP BINDING TO MOUSE COLON CANCER (MC-26) CELLS AND NORMAL COLON MUCOSAL IN THE PRESENCE OF BOMBESIN RECEPTOR ANTAGONISTS

| | $IC_{50}$(nM) |
|---|---|
| Colon Cancer (MC-26) Cells | |
| BBS | 0.8 |
| BIM-26147: Phe$^6$-BBS (6–13) Propylamide | 4.5 (5.6-fold) |
| Leu$^{13}$-ψ(CH$_2$, NH)-Leu$^{14}$-BBS | 80 (100-fold) |
| Normal Colon Mucosal | |
| BBS | 0.14 |
| BIM-26147: Phe$^6$-BBS (6,13) Propylamide | 1.60 (11-4-fold) |
| Leu$^{13}$-ψ(CH$_2$NH)-Leu$^{14}$-BBS | 15 (107-fold) |

TABLE 2

RESPONSE OF THE CX-5 HUMAN COLON ADENOCARCINOMA TO BOMBESIN ANTAGONIST [D-Cpa 6, Y Leu, Phe 14} BN(6–14) NH$_2$ (BIM-26159): 11-DAY SRCA

| | | BL89-128 | |
|---|---|---|---|
| Group No. | Treatment | Change in Tumor Size$^1$ (omu) | % Test/Control$^2$ |
| 1 | Saline vehicle control, 0.2 ml, i.p., b.i.d., QD1-10 | 8.67 ± 0.42 | — |
| 2 | BIM-26159, 10 µg/inj., i.p., b.i.d., QD1-10 | 5.60 ± 0.84** | 64 |
| 3 | BIM-26159, 50 µg/inj., i.p., b.i.d., QD1-10 | 6.10 ± 1.18* | 70 |
| 3 | BIM-26159, 250 µg/inj., i.p., b.i.d., QD1-10 | 6.17 ± 1.56 | 71 |

$^1$Change in tumor size between day 0 and day 11 in ocular micrometer units (omu) presented as means ± S.E.M. Significance of difference from control Student's t Test: **p < 0.01, *p < 0.05
$^2$% Test/Control = Test tumor size/Control number size × 100

TABLE 3

RESPONSE OF THE CX-5 HUMAN COLON ADENOCARCINOMA TO BOMBESIN ANTAGONIST [D-Cpa 6, Y Leu, Phe 14} BN(6–14) NH$_2$ (BIM-26159): 11-DAY SRCA

| | | BL89-130 | |
|---|---|---|---|
| Group No. | Treatment | Change in Tumor Size$^1$ (omu) | % Test/Control$^2$ |
| 1 | Saline vehicle control, 0.2 ml, i.p., b.i.d., q.d. 1-10 | 7.08 ± 0.92 | — |
| 2 | BIM-26159, 50 µg/inj., s.c., b.i.d., q.d. 1-10 | 1.83 ± 0.91** | 26 |
| 3 | BIM-26159, 250 µg/inj., s.c., b.i.d., q.d. 1-10 | 4.67 ± 1.41 | 66 |
| 4 | BIM-26159, 50 µg/inj., i.p., b.i.d., q.d. 1-10 | 3.20 ± 1.45* | 45 |

$^1$Change in tumor size between day 0 and day 11 in ocular micrometer units (omu) presented as means ± S.E.M. Significance of difference from control Student's t Test: **p < 0.01, *p < 0.05
$^2$% Test/Control = Test tumor size/Control number size × 100

TABLE 4

RESPONSE OF THE MCF-7 HUMAN BREAST TUMOR TO BOMBESIN ANTAGONIST (BIM-26159) [D-p-Cl-Phe$^6$, Leu$^{13}$ψ[CH$_2$NH]Phe$^{14}$NH$_2$] BN(6–14) NH$_2$ AND SOMATOSTATIN ANALOGUE BIM-23014C: 15-DAY SRCA

| Group No. | Treatment | Change in Tumor Size$^1$ (omu) | % Test/Control$^2$ |
|---|---|---|---|
| 1 | E$_2$ implanted saline vehicle control, 0.2 ml, i.p., b.i.d., q.d. 1-14 | 1.07 ± 1.18 | — |
| 2 | E$_2$ unimplanted saline vehicle control, 0.2 ml, i.p., b.i.d., q.d. 1-14 | −6.81 ± 1.01*** | R600 |
| 3 | E$_2$ BIM-26159, 250 µg/inj., i.p. b.i.d., q.d. 1-14 | −1.38 ± 0.74 | R129 |
| 4 | E$_2$ + BIM-23014C, 500 µg/inj., s.c., b.i.d. q.d. 1-14 | 0.13 ± 0.78 | 12 |

$^1$Change in tumor size between day 0 and day 15 in ocular micrometer units (omu) presented as means ± S.E.M. Difference from control: ***p < 0.001
$^2$% Test/Control = Test tumor size/Control tumor size × 100

TABLE 5

RESPONSE OF THE 13762NF RAT MAMMARY ADENOCARCINOMA TO BOMBESIN ANALOG (BIM-26159): [D-p-Cl-Phe⁶, Leu¹³ψ[CH₂NH]Phe¹⁴-NH₂] BN(6-14): 7-DAY SRCA

| Group No. | Treatment | Change in Tumor Size[1] (omu) | % Test/Control[2] |
|---|---|---|---|
| 1 | Saline vehicle control, 0.2 ml, i.p., b.i.d., q.d. 1-6 | 13.4 ± 187 | — |
| 2 | BIM-26159, 250 μg/inj., i.p., b.i.d., q.d. 1-6 | 11.17 ± 2.70 | 83 |
| 3 | BIM-26159, 50 μg/inj., s.c., b.i.d., q.d. 1-6 | 12.88 ± 2.67 | 96 |
| 4 | BIM-26159, 10 μg/inj., s.c., b.i.d., q.d. 1-6 | 17.20 ± 1.23 | 128 |

[1]Change in tumor size between day 0 and day 7 in ocular micrometer units (omu) presented as means ± S.E.M.
[2]% Test/Control = Test tumor size/Control tumor size × 100

TABLE 6

RESPONSE OF THE 13762NF RAT MAMMARY ADENOCARCINOMA TO THE BOMBESIN ANALOG BIM-26147 [D-Phe⁶, Leu¹³, (des-Met¹⁴) PROPYLAMIDE]BN(6-14): SUBCUTANEOUS ASSAY ON DAY 9

| Group No. | Treatment | Lag Time[1] (Days) | Tumor Size (mm)[2] Day 9 | % Test/ Control |
|---|---|---|---|---|
| 1 | Vehicle treated control, 0.2 ml/inj., s.c., b.i.d., q.d. 1-9 | 9.5 | 5.6 ± 1.1 | — |
| 2 | BIM-26147, 250 μg/inj., s.c., b.i.d., q.d. 1-9 | 11.3 | 3.4 ± 1.8 | 61 |
| 3 | BIM-26147, 50 μg/inj., s.c., b.i.d., q.d. 1-9 | 8.6 | 6.9 ± 0.24 | 123 |
| 4 | BIM-26147, 50 μg/inj., s.c., as an infusion, b.i.d., q.d. 1-9 | 10.0 | 4.9 ± 1.6 | 87 |

[1]Lag Time: Number of days post implantation to reach a size of approximately 5.0 mm average diameter.
[2]Data reported as means ± s.e.m.

TABLE 7

RESPONSE OF THE 13762NF RAT MAMMARY ADENOCARCINOMA TO BOMBESIN ANALOG BIM-26147 [D-Phe⁶, Leu¹³, (des-Met¹⁴) PROPYLAMIDE]BN(6-14): SUBCUTANEOUS ASSAY ON DAY 15

| Group No. | Treatment | Tumor Size[1] 15 (mm) Treatment Day | % Test/Control[2] |
|---|---|---|---|
| 1 | Vehicle treated control, 0.2 ml/inj., s.c., b.i.d., q.d. 1-14 | 18.2 ± 2.00 | — |
| 2 | BIM-26147, 250 μg/inj., s.c., b.i.d., q.d. 1-14 | 15.2 ± 3.35 | 83 |
| 3 | BIM-26147, 50 μg/inj., s.c., b.i.d., q.d. 1-14 | 20.07 ± 1.83 | 114 |
| 4 | BIM-26147, 50 μg/inj., s.c. infusion, b.i.d., q.d. 1-14 | 18.3 ± 3.46 | 100 |

[1]Tumor size = (Length + Width/2) mm, reported as means S.E.M.

TABLE 8

RESPONSE OF THE MT/W9A-R MAMMARY CARCINOMA TO BOMBESIN ANALOG [D-p-Cl-Phe⁶, Leu¹³ψ[CH₂NH]Phe¹⁴-NH₂] BN(6-14) (BIM-26159): 11-DAY SRCA

| Group No. | Treatment | Tumor Size[1] Day 14 (mm) | % Test/Control[2] |
|---|---|---|---|
| 1 | Saline vehicle control, 0.2 ml, i.p., b.i.d., q.d. 1-6 | 22.9 ± 2.06 | — |
| 2 | BIM-26159, 250 μg/inj. | 23.9 ± 3.72 | 104 |

TABLE 8-continued

RESPONSE OF THE MT/W9A-R MAMMARY CARCINOMA TO BOMBESIN ANALOG [D-p-Cl-Phe⁶, Leu¹³ψ[CH₂NH]Phe¹⁴-NH₂] BN(6-14) (BIM-26159): 11-DAY SRCA

| Group No. | Treatment | Tumor Size[1] Day 14 (mm) | % Test/Control[2] |
|---|---|---|---|
|  | i.p., b.i.d., q.d. 1-10 |  |  |
| 3 | BIM-26159, 150 μg/inj., i.p., b.i.d., q.d. 1-10 | 16.7 ± 1.91* | 73 |
| 4 | BIM-26159, 10 μg/inj., i.p., b.i.d., q.d. 1-10 | 24.5 ± 2.68 | 107 |

[1]Change in tumor size between day 0 and day 7 in ocular micrometer units (omu) presented as means ± S.E.M. Significance of difference from control *p < 0.05.
[2]% Test/Control = Test tumor size/Control tumor size × 100

TABLE 9

SUMMARY OF BREAST TUMOR SCREENING RESULTS WITH BOMBESIN ANALOGS

| Breast Tumor | Species | Type of Assay | Bombesin Analog | Tumor Response* |
|---|---|---|---|---|
| MCF-7 | Human | 15-Day SCRA | BIM-26159 | + |
|  |  | 20-Day SCRA | BIM-26187 | + |
| 13762NF | Rat | 7-Day SCRA | BIM-26159 | + |
|  |  | 14-Day SCRA (Days 9, 14) | BIM-26147 | + |
| MT/W9A-4 | Rat | 11-Day SCRA | BIM-26159 | + |

*Responses: + Tumor inhibition

We claim:

1. A method of treating colon, prostate of breast cancer in a mammal by administering to said mammal an effective amount of a peptide, wherein said peptide is a peptide comprising between eight and ten amino acid residues, inclusive, said peptide being an analog of one of the following naturally occurring peptides which terminate at the carboxy-terminus with a Met residue: (a) litorin; (b) the ten amino acid carboxy-terminal region of mammalian GRP, neuromedin B, or neuromedin C; and (c) the ten amino acid carboxy-terminal region of amphibian bombesin, said analog being of the formula:

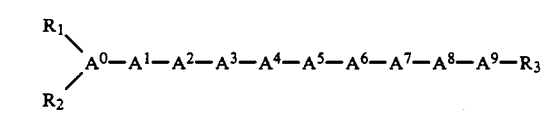

wherein
$A^0$ = pGlu, Gly, Nle, α-aminobutyric acid, or the D-isomer of any Ala, Val, Gln, Asn, Leu, Ile, p-X-Phe (where X=H, F, Cl, Br, NO₂, OH, CH₃), Trp, or β-Nal, or is deleted;
$A^1$ = the D or L-isomer of any of pGlu, Nle, or α-aminobutyric acid, or the D-isomer of any of Ala, Val, Gln, Asn, Leu, Ile, p-X-Phe (where X=H, F, Cl, Br, NO₂, OH, or CH₃), F₅-Phe, Trp, or β-Nal, or is deleted;
$A^2$ = pGlu, Gly, Ala, Val, Gln, Asn, Leu, Ile, p-X-Phe (where X=H, F, Cl, Br, NO₂, OH, or CH₃), Trp, β-Nal, His, 1-methyl-His or 3-methyl-His;
$A^3$ = the D or L isomer of any of p-X-Phe (where X=H, F, Cl, Br, NO₂, OH, or CH₃), β-Nal, or Trp;
$A^4$ = Ala, Val, Gln, Asn, Gly, Leu, Ile, Nle, α-aminobutyric acid, p-X-Phe (where X=H, F, Cl, Br, NO₂, OH, or CH₃), Trp, or β-Nal;

$A^5$ = Gln, Asn, Gly, Ala, Leu, Ile, Nle, α-aminobutyric acid, Val, p-X-Phe (where X=H, F, Cl, Br, $NO_2$, OH, or $CH_3$), Trp, Thr, or β-Nal;
$A^6$ = Sar, Gly or the D-isomer of any Ala, N-methyl-Ala, Val, Gln, Asn, Leu, Ile, p-X-Phe (where X=H, F, Cl, Br, $3NO_2$, OH, or $CH_3$), Trp, Cys, or β-Nal;
$A^7$ = 1-methyl-His, 3-methyl-His, or His;
$A^8$ = Leu, Ile, Val, Nle, α-aminobutyric acid, p-X-Phe (where X=H, F, Cl, Br, $NO_2$, OH, or $CH_3$), Trp, Thr, or β-Nal;
$A^9$ = L-isomer of any of Met, Met-oxide, Leu, Ile, Nle, α-aminobutyric acid, p-X-Phe (where X=H, F, Cl, Br, $NO_2$, OH, or $CH_3$), Trp, or β-Nal; each $R_1$ and $R_2$, independently, is H, $C_{1-12}$ alkyl, $C_{7-10}$ phenylalkyl, $COE_2$ (where $E_1$ is $C_{1-20}$ alkyl, $C_{3-20}$ alkenyl, $C_{3-20}$ alkynyl, phenyl, naphthyl, or $C_{7-10}$ phenylalkyl), or $C_1$–$C_{12}$ acyl, and $R_1$ and $R_2$ are bonded to the N-terminal amino acid of the peptide; provided that when one of $R_1$ or $R_2$ is $COE_1$, the other must be H; and $R_3$ is H, $NH_2$, $C_{1-12}$ alkyl, $C_{7-10}$ phenylalkyl, or $C_{3-20}$ naphthylalkyl; and further provided that, if $A^0$ is present, $A^1$ cannot be pGlu; and, if $A^0$ or $A^1$ is present, $A^2$ cannot be pGlu; and further provided that, when $A^0$ is deleted and $A^1$ is pGlu; $R_1$ must be H and $R_2$ must be the portion of Glu that forms the imine ring in pGlu; and for each of the residues $A^6$, $A^7$, $A^8$, and $A^9$, independently, the carbon atom participating in the amide bond between that residue and the nitrogen atom of the alpha amino group of the adjacent amino acid residue may be a carbonyl carbon or may be reduced to a methylene carbon, or a pharmaceutically acceptable salt thereof.

2. The method of claim 1, said analog comprising the formula:
$A^0$ = pGlu, Gly, D-Phe, or is deleted;
$A^1$ = pGlu, D-Phe, D-Ala, D-β-Nal, D-Cpa, D-Asn, Cys, or is deleted;
$A^2$ = pGlu, Asn, Gln, His, 1-methyl-His, 3-methyl-His, Cys or is deleted;
$A^3$ = Trp;
$A^4$ = Ala;
$A^5$ = Val;
$A^6$ = Sar, Gly, D-Phe, or D-Ala;
$A^7$ = His;
$A^8$ = Leu, Phe, Chx-Ala, or Cys;
$A^9$ = L-isomer of any of Met, Leu, Ile, Nle, Phe, or Cys.

3. The method of claim 2, wherein said analog is of the amino acid formula pGlu-Gln-Trp-Ala-Val-Gly-His-Leu-Leu-$NH_2$.

4. The method of claim 2, wherein said analog is of the amino acid formula:

D-Phe-Gln-Trp-Ala-Val-Gly-His-Leu-Leu-$NH_2$.

5. The method of claim 2, wherein said analog is of the amino acid formula:

D-Phe-Gln-Trp-Ala-Val-Gly-His-Leu-Met-$NH_2$.

6. The method of claim 2, wherein said analog is of the amino acid formula:

D-Cpa-Gln-Trp-Ala-Val-Gly-His-Leu-Met-$NH_2$.

7. The method of claim 2, wherein said analog is of the amino acid formula:

D-Cpa-Gln-Trp-Ala-Val-Gly-His-Leu-Leu-$NH_2$.

8. The method of claim 2, wherein said analog is of the amino acid formula:

D-Phe-Gln-Trp-Ala-Val-D-Ala-His-Leu-Leu-$NH_2$.

9. The method of claim 2, wherein said analog is of the amino acid formula:

D-Phe-Gln-Trp-Ala-Val-D-Ala-His-Leu-Met-$NH_2$.

10. The method of claim 2, wherein said analog is of the amino acid formula:

D-Cpa-Gln-Trp-Ala-Val-D-Ala-His-Leu-Met-$NH_2$.

11. The method of claim 2, wherein said analog is of the amino acid formula:

pGlu-Gln-Trp-Ala-Val-Gly-His-Phe-Leu-$NH_2$.

12. The method of claim 2, wherein said analog is of the amino acid formula:

D-Phe-Gln-Trp-Ala-Val-Gly-His-Phe-Leu-$NH_2$.

13. The method of claim 2, wherein said analog is of the amino acid formula:

D-Phe-Gln-Trp-Ala-Val-D-Ala-His-Phe-Met-$NH_2$.

14. The method of claim 2, wherein said analog is of the amino acid formula:

D-Phe-Gln-Trp-Ala-Val-D-Ala-His-Phe-Leu-$NH_2$.

15. The method of claim 2, wherein said analog is of the amino acid formula:

D-Phe-Gln-Trp-Ala-Val-Gly-His-Leu-Nle-$NH_2$.

16. The method of claim 2, wherein said analog is of the amino acid formula:

D-Phe-Gln-Trp-Ala-Val-D-Ala-His-Leu-Nle-$NH_2$.

17. The method of claim 2, wherein said analog is of the amino acid formula:

D-Phe-Gln-Trp-Ala-Val-Gly-His-Phe-Nle-$NH_2$.

18. The method of claim 2, wherein said analog is of the amino acid formula:

D-Phe-Gln-Trp-Ala-Val-D-Ala-His-Phe-Nle-$NH_2$.

19. The method of claim 2, wherein said analog is of the amino acid formula:

Ac-His-Trp-Ala-Val-D-Ala-His-Leu-Leu-$NH_2$.

20. The method of claim 2, wherein said analog is of the amino acid formula:

D-Phe-Gln-Trp-Ala-Val-Gly-His-CHx-Ala-Leu-$NH_2$.

21. The method of claim 2, wherein said analog is of the amino acid formula:

cyclo—D—Phe—Gln—Trp—Ala—Val—Gly—His—Leu—Leu;

22. The method of claim 2, wherein said analog is of the amino acid formula:

D—Cys—Asn—Trp—Ala—Val—Gly—His—Leu—Cys—NH$_2$;

23. The method of claim 2, wherein said analog is of the amino acid formula:

cyclo—His—Trp—Ala—Val—Gly—His—Leu—Met;

24. The method of claim 2, wherein said analog is of the amino acid formula:

Cys—Trp—Ala—Val—Gly—His—Leu—Cys—NH$_2$;

25. The method of claim 2, wherein said analog is of the amino acid formula:

cyclo—D—Phe—Gln—Trp—Ala—Val—Gly—His—Leu—Met;

26. The method of claim 3, wherein said analog is of the amino acid formula:

cyclo—D—Phe—His—Trp—Ala—Val—Gly—His—Leu—Met;

27. The method of claim 2, wherein said analog is of the amino acid formula:

cyclo—Trp—Ala—Val—Gly—His—Leu—Met;

28. A method of treating colon, prostate or breast cancer in a mammal by administering to said mammal an effective amount of a peptide, wherein said analog administered according to methods of the invention comprises a peptide comprising between seven and ten amino acid residues, inclusive, and is an analog of one of the following naturally occurring peptides terminating at the carboxy-terminus with a Met residue: (a) litorin; (b) the ten amino acid carboxy-terminal region of mammalian GRP, neuromedin B, or neuromedin C; and (c) the ten amino acid carboxy-terminal region of amphibian bombesin, said analog being of the following formula:

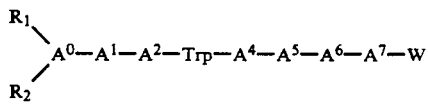

wherein
$A^0$=pGlu, Gly, Nle, α-aminobutyric acid, or the D-isomer of any of Ala, Val, Gln, Asn, Leu, Ile, Met, p-X-Phe (where X=F, Cl, Br, NO$_2$, OH, H or CH$_3$), Trp, Cys, or β-Nal, or is deleted;

$A^1$=the D or L-isomer of any of pGlu, Nle, α-aminobutyric acid, or the D-isomer of any of Ala, Val, Gln, Asn, Leu, Ile, Met, p-X-Phe (where X=F, Cl, Br, NO$_2$, OH, H or CH$_3$), F$_5$-Phe, Trp, Cys, or β-Nal, or is deleted;

$A^2$=pGlu, Gly, Ala, Val, Gln, Asn, Leu, Ile, Met, p-X-Phe (where X=F, Cl, Br, NO$_2$, OH, H or CH$_3$), Trp, Cys, β-Nal, His, 1-methyl-His, or 3-methyl-His;

$A^4$=Ala, Val, Gln, Asn, Gly, Leu, Ile, Nle, α-aminobutyric acid, Met, p-X-Phe (where X=F, Cl, Br, NO$_2$, OH, H or CH$_3$), Trp, Cys, or β-Nal;

$A^5$=Gln, Asn, Gly, Ala, Leu, Ile, Nle, α-aminobutyric acid, Met, Val, p-X-Phe (where X=F, Cl, Br, OH, H or CH$_3$), Trp, Thr, or β-Nal;

$A^6$=Sar, Gly, or the D-isomer of any of Ala, N-methyl-Ala, Val, Gln, Asn, Leu, Ile, Met, p-X-Phe (where X=F, Cl, Br, NO$_2$, OH, H or CH$_3$), Trp, Cys, or β-Nal;

$A^7$=1-methyl-His, 3-methyl-His, or His;

provided that, if $A^0$ is present, $A^1$ cannot be pGlu; further provided that, if $A^0$ or $A^1$ is present, $A^2$ cannot be pGlu; further provided that, when $A^0$ is deleted and $A^1$ is pGlu, $R_1$ must be H and $R_2$ must be the portion of Glu that forms the imine ring in pGlu; and further provided that, W can be any one of the following:

(I):

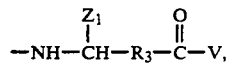

wherein $R_3$ is CHR$_{20}$—(CH$_2$)$_{n1}$ (where R$_{20}$ is either of H or OH; and n1 is either of 1 or 0), or is deleted, and $Z_1$ is the identifying group of any of the amino acids Gly, Ala, Val, Leu, Ile, Ser, Asp, Asn, Glu, Gln, p-X-Phe (where X=H, F, Cl, Br, NO$_2$, OH, or CH$_3$), F$_5$-Phe, Trp, Cys, Met, Pro, HyPro, cyclohexyl-Ala, or β-nal, and V is either

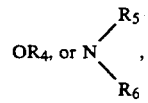

where R$_4$ is any of C$_{1-20}$ alkyl, C$_{3-20}$ alkenyl, C$_{3-20}$ alkynyl, phenyl, naphthyl, or C$_{7-10}$ phenylalkyl, and each R$_5$, and R$_6$, independently, is any of H, C$_{1-12}$ alkyl, C$_{7-10}$ phenylalkyl, lower acyl, or,

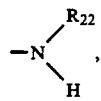

where R$_{22}$ is any of H, C$_{1-12}$ alkyl, C$_{7-10}$ phenylalkyl, or lower acyl; provided that, when one of R$_5$ or R$_6$ is —NHR$_{22}$, the other is H;

(II):

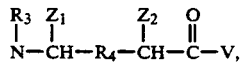

wherein R$_4$ is CH$_2$—NH, CH$_2$—S, CH$_2$—O, CO—CH$_2$, CH$_2$—CO, or CH$_2$—CH$_2$, and each Z$_1$ and Z$_2$, independently, is the identifying group of any one of the amino acids Gly, Ala, Val, Leu, Ile, Ser, Asp, Asn, Glu, Gln, $\beta$-Nal, p-X-Phe (where X=H, F, Cl, Br, $NO_2$, OH or $CH_3$), $F_5$-Phe, Trp, Cys, Met, Pro, HyPro, or cyclohexyl-Ala; and V is either $OR_5$ or

where each $R_3$, $R_5$, $R_6$, and $R_7$, independently, is H, lower alkyl, lower phenylalkyl, or lower naphthylalkyl;

(III):

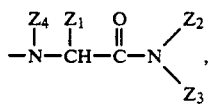

wherein $Z_1$ is the identifying group of any one of the amino acids Gly, Ala, Val, Leu, Ile, Ser, Asp, Asn, Glu, $\beta$-Nal, Gln, p-X-Phe (where X=H, F, Cl, Br, $NO_2$, OH or $CH_3$), $F_5$-Phe, Trp, Cys, Met, Pro, or HyPro; and each $Z_2$, $Z_3$, and $Z_4$, independently, is H, lower alkyl, lower phenylalkyl, or lower naphthylalkyl; or (IV):

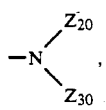

wherein each $Z_{20}$ and $Z_{30}$, independently, is H, lower alkyl, lower phenylalkyl, lower naphthylalkyl; further provided that, when either of $Z_{20}$ or $Z_{30}$ is other than H, $A^7$ is His, $A^6$ is Gly, $A^5$ is Val, $A^4$ is Ala, $A^2$ is His, and either of $R_1$ or $R_2$ is other than H, $A^1$ must be other than deleted; further provided that, for the formulas (I) through (IV), any asymmetric carbon atom can be R, S or a racemic mixture; and further provided that each $R_1$ and $R_2$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkynyl, phenyl, naphthyl, or $C_{7-10}$ phenylalkyl), or lower acyl, and $R_1$ and $R_2$ are bonded to the N-terminal amino acid of said peptide, and further provided that when one of $R_1$ or $R_2$ is $COE_1$, the other must be H, or a pharmaceutically acceptable salt thereof.

29. The method of claim 28 wherein said analog is of the formula
$A^0$=Gly, D-Phe, or is deleted;
$A^1$=p-Glu, D-Phe, D-Ala, D-$\ominus$-Nal, D-Cpa, or D-Asn;
$A^2$ Gln, His, 1-methyl-His, or 3-methyl-His;
$A^4$=Ala;
$A^5$=Val;
$A^6$=Sar, Gly, D-Phe, or D-Ala;
$A^7$=His;
and, where W is (I) and $R_3$ is $CH_2$ or $CH_2$—$CH_2$, $Z_1$ is the identifying group of Leu or Phe, where W is (I) and $R_3$ is $CHOH$-$CH_2$, $Z_1$ is the identifying group of Leu, cyclohexyl-Ala, or Phe and each $R_5$ and $R_6$ is H; and where W is (I), V is $NHR_6$, and $R_6$ is $NH_2$; where W is (II) and $R_4$ is $CH_2$—NH each $Z_1$ is the identifying group of Leu, or Phe, and $Z_2$ is the identifying group of Leu or Phe; where W is (III), $Z_1$ is the identifying group of any one of the amino acids Leu or p-X-Phe (where X=H, F, Cl, Br, $NO_2$, OH or $CH_3$); and each $Z_2$, $Z_3$ and $Z_4$, independently, is H, lower alkyl, lower phenylalkyl, or lower naphthylalkyl; and where W is (IV), each $Z_{20}$ and $Z_{30}$, is H; and each $R_1$ and $R_2$, independently, is H, lower alkyl, or lower acyl.

30. The method of claim 29 wherein said analog is of the amino acid formula:

D-$\beta$-Nal-Gln-Trp-Ala-Val-Gly-His-Leu$\Psi$[$CH_2NH$]-Phe-$NH_2$.

31. The method of claim 29 wherein said analog is of the amino acid formula:

D-Phe-Gln-Trp-Ala-Val-Gly-His-Leu-ethylamide.

32. The method of claim 29 wherein said analog is of the amino acid formula:

p-Glu-Gln-Trp-Ala-Val-Gly-His-statine-amide.

33. The method of claim 29 wherein said analog is of the amino acid formula:

D-Cpa-Gln-Trp-Ala-Val-Gly-His-$\beta$-Leu-$NH_2$.

34. The method of claim 29 wherein W is (II), $R_4$ is $CH_2$—NH, and said carbon atom bonded to $Z_2$ is of said R configuration.

35. The method of claim 34, wherein said analog is of the amino acid formula:

D-Cpa-Gln-Trp-Ala-Val-D-Ala-His-$\beta$-Leu-$NH_2$.

36. The method of claim 29, wherein said analog is of the amino acid formula:

D-Cpa-Gln-Trp-Ala-Val-Gly-His-Leu$\Psi$[$CH_2NH$]-Phe-$NH_2$.

37. The method of claim 29, said analog is of the amino acid formula:

D-Phe-Gln-Trp-Ala-Val-Gly-His-Leu-propylamide.

38. The method of claim 34 wherein said analog is of the amino acid formula:

D-Phe-Gln-Trp-Ala-Val-Gly-His-Leu$\Psi$[$CH_2NH$]-D-Phe-$NH_2$.

39. The method of claim 28 wherein W is (I), V is $OR_4$, and $R_4$ is any of $C_{1-20}$ alkyl, $C_{3-20}$ alkenyl, $C_{3-20}$ alkinyl, phenyl, naphthyl, or $C_{7-10}$ phenylalkyl, and $A^6$ is N-methyl-D-Ala or $A^1$ is D-$F_5$-Phe.

40. The method of claim 39 wherein said analog is of the amino acid formula:

D-Phe-Gln-Trp-Ala-Val-N-methyl-D-Ala-His-Leu-methylester.

41. The method of claim 39 wherein said analog is of the amino acid formula:

D-$F_5$-Phe-Glu-Trp-Ala-Val-D-Ala-His-Leu-methylester.

* * * * *

UNITED STATES PATENT AND TRADEMARK OFFICE
CERTIFICATE OF CORRECTION

PATENT NO. : 5,217,955

DATED : June 8, 1993

INVENTOR(S) : Authur E. Bogden, et al

It is certified that error appears in the above-indentified patent and that said Letters Patent is hereby corrected as shown below:

Column 4, line 63: delete "deletd" and replace it with --deleted--.

Column 9, line 21: delete "Glu" and replace it with --Gln--.

Column 10, line 34: delete "Mol" and replace it with --Mol.--.

Column 15, line 25: delete "chlrodie" and replace it with --chloride--.

Column 16, line 27: delete "treaed" and replace it with --treated--.

Column 29, line 55: delete "D-θ-Nal" and replace it with --D-β-Nal--.

Column 30, line 65: delete "Glu" and replace it with --Gln--.

UNITED STATES PATENT AND TRADEMARK OFFICE
CERTIFICATE OF CORRECTION

PATENT NO. : 5,217,955
DATED : June 8, 1993
INVENTOR(S) : Authur E. Bogden, et al It is certified that error appears in the above-indentified patent and that said Letters Patent is hereby corrected as shown below:

Column 15, line 25, "eg" should read --eq--.

Signed and Sealed this

Sixteenth Day of August, 1994

Attest:

BRUCE LEHMAN

Attesting Officer

Commissioner of Patents and Trademarks